United States Patent [19]

Vlattas

[11] 4,041,047
[45] Aug. 9, 1977

[54] 9-THIAPROSTAGLANDINS

[75] Inventor: Isidoros Vlattas, Summit, N.J.

[73] Assignee: Ciba-Geigy Corporation, Ardsley, N.Y.

[21] Appl. No.: 621,901

[22] Filed: Oct. 14, 1975

Related U.S. Application Data

[63] Continuation-in-part of Ser. No. 516,293, Oct. 21, 1974, Pat. No. 3,970,670, which is a continuation-in-part of Ser. No. 460,837, April 15, 1974, abandoned, which is a continuation-in-part of Ser. No. 361,752, May 18, 1973, Pat. No. 3,881,017.

[51] Int. Cl.$^2$ .......................................... C07D 333/48
[52] U.S. Cl. ................................. 260/332.1; 424/275
[58] Field of Search ...................... 260/332.1, 332.2 A

[56] References Cited

PUBLICATIONS

Vlattas, et al., "Tetrahedron Letters," No. 51/52, pp. 4459–4462, (1974).

Primary Examiner—James O. Thomas, Jr.
Assistant Examiner—A. Siegel
Attorney, Agent, or Firm—Joseph G. Kolodny; Theodore O. Groeger; John J. Maitner

[57] ABSTRACT

7-[3α-(3-hydroxy-3-hydrocarbylpropyl, or -1-propenyl, or 1-propynyl)-4-hydroxy-tetrahydro-2β-thienyl]-heptanoic or 5-heptenoic acids, sulfoxides, sulfones, esters or salts thereof are stable, prostaglandin-like acting and antiasthmatic agents.

7 Claims, No Drawings

9-THIAPROSTAGLANDINS

CROSS-REFERENCE TO RELATED APPLICATIONS

This is a continuation-in-part of application Ser. No. 516,293, filed Oct. 21, 1974, (now U.S. Pat. No. 3,970,670) which in turn is a continuation-in-part of application Ser. No. 460,837, filed Apr. 15, 1974, (now abandoned) which in turn is a continuation-in-part of application Ser. No. 361,752, filed May 18, 1973 (now U.S. Pat. No. 3,881,017).

SUMMARY OF THE INVENTION

The present invention concerns and has for its object the provision of new 7-[3αO(3-hydroxy-3-hydrocarbyl-propyl or -1-propen- or ynyl)-4-hydroxy-tetrahydro-2β-thienyl]-alkanoic or 5-alkenoic acids, particularly of those corresponding to formula I

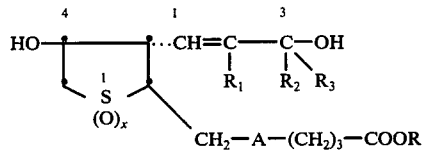

wherein R is hydrogen, one base-equivalent or an aliphatic, cycloaliphatic, araliphatic or aromatic radical, A is methylene, ethylene or ethenylene, each of $R_1$ and $R_2$ is hydrogen or lower alkyl, $R_3$ is an aliphatic, cycloaliphatic or araliphatic radical and x is an integer from 0 to 2, or the 1,2-dihydro or -dehydro derivatives thereof, corresponding pharmaceutical compositions and methods for the preparation and application of these products, which are useful prostaglandin- like acting smooth muscle contractants and antiasthmatic agents, but more stable than the easily dehydrating prostaglandins of the E series.

DESCRIPTION OF THE PREFERRED EMBODIMENTS

An aliphatic radial R or $R_3$ represents preferably lower alkyl, as is the case with $R_1$ and $R_2$, e.g. methyl, ethyl, n- or i-propyl, -butyl, -pentyl, -hexyl or -heptyl; lower alkenyl e.g. allyl or methallyl; or lower alkynyl, e.g. ethynyl or propargyl. The term "lower" referred to above and hereinafter in connection with organic radicals or compounds respectively, defines such with up to 7, preferably up to 4, carbon atoms. $R_3$ also represents higher alkyl, especially such with 8 to 12 carbon atoms, such as n- or i-octyl, -nonyl, -decyl, -undecyl or -dodecyl.

Said lower cycloaliphatic radicals R and $R_3$ are preferably 3 to 7 ring-membered cycloalkyl, cycloalkenyl or (cycloalkyl or cycloalkenyl)-lower alkyl groups, e.g. cyclopropyl, cyclobutyl, cyclopentyl or cyclohexyl; cyclopent-1-enyl or cyclohex-1 or 3-enyl; cyclopropylmethyl, cyclobutylmethyl, 1- or 2-cyclopentylethyl; cyclopent-3-enylmethyl or cyclohex-1-enylmethyl.

Said araliphatic or aromatic radicals R or $R_3$ are preferably isocyclic, monocyclic radicals, such as phenyl-lower alkyl or phenyl groups, unsubstituted or substituted in the aromatic ring by one or more than one, especially one or two, of the same or different substituents, such as lower alkyl, e.g. methyl, ethyl, n- or i-propyl or -butyl; lower alkoxy, e.g. methoxy, ethoxy, n-or i-propoxy or -butyoxy; lower alkylenedioxy, e.g. methylenedioxy, 1,1- or 1,2-ethylenedioxy; halogeno, e.g. fluoro, chloro, bromo or iodo; trifluoromethyl; nitro or amino, such as di-lower alkylamino, e.g. dimethylamino or diethylamino. Said aliphatic radicals, especially lower alkyl groups $R_3$, can also be substituted by one of said lower alkoxy groups or one, or up to the maximum number of halogen atoms, as is the case in trifluoromethyl, 2-(methoxy, ethoxy, chloro, bromo or iodo)-ethyl, -propyl or -butyl, 2,2-dichloro-ethyl, -propyl or -butyl, 2,2,2-trichloroethyl, 3-(methoxy, ethoxy, chloro or bromo)-propyl or -butyl, 4-(methoxy or chloro)-butyl.

The compounds of the invention exhibit valuable, prostaglandin-like properties, especially smooth muscle contracting and antiasthmatic activity. This can be demonstrated either in vitro or *in vivo* tests, using advantageously mammals, such as mice, rats, guinea pigs or dogs as test objects, or isolated organs thereof. The *in vitro* tests are performed with the guinea pig ileum in a standard organ bath, e.g. physiological saline. The compounds of the invention, when added to said bath in such amounts to reach concentrations down to about $10^{-8}$ molar, contract the isolated ileum. Histamine hydrochloride and prostaglandin $E_1$ are used as a positive standard and the usual experiments include the control for vehicle and buffer effects.

Antiasthmatic activity is estimated in dogs, who are natually sensitive to ascaris antigens, causing asthma-like syndroms after inhalation of said nebulized antigens. The compounds of the invention are administered intravenously 30–60 minutes after antigen-challenge and efficacy is estimated by the change in respiratory-rate and airway-resistance.

Moreover, anti-fertility effects are tested in rats or hamsters, e.g. by administering the compounds of the invention to pregnant hamsters, for example 2.5 to 10 mg/kg thereof, subcutaneously once on day five of pregnancy, and inspecting on the eleventh day the uterus thereof for implantation sites and surviving embryos. Also smaller doses can be used for intravenous or intrauterine administration, or larger amounts for oral administration, e.g. to spontaneous hypertensive rates, whose blood pressure is monitored by standard means, and is reduced by said compounds.

Accordingly, the compounds of the invention can be applied enterally or parenterally, e.g. by inhalation of a nebulized aqueous solution, or by peroral, subcutaneous, intramuscular, intraveneous or intrauterine administrtion, in the dosage range known for the natural prostaglandins. According to the test results obtained, they are useful antiasthmatic, hypotensive, abortifacient and luteolytic agents, for example, in the treatment or management of hypertension, especially fertility. They are also valuable intermediates of other preparations, preferably of pharmacologically useful products.

Preferred compounds of the invention are those of Formula I, in which each of R and $R_3$ is alkyl with up to 12 carbon atoms, lower alkenyl, lower alkynyl, (3 to 7-ring-membered cycloalkyl or cycloalkenyl)-$C_mH_{2m}$ wherein m is an integer from 0 to 4, or Ph-$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)-phenyl, (nitro)-phenyl or (di-lower alkylamino)-phenyl and n is an integer from 1 to 4, R is also hydrogen, Ph, an alkali metal, one equivalent of an alkaline earth metal, ammonium, mono-, di- or tri- lower (alkyl or mono-, di- or trihydroxyalkyl)- ammonium and $R_3$ is also (lower alkoxy or halo)-lower alkyl, A is ethylene or ethenylene, $R_1$ and $R_2$ are hydrogen or lower alkyl, or the 1,2-dihydro-derivatives thereof, and $x$ is 0 to 2, or the 1,2-dehydro-derivatives thereof.

More active and stable are those $3\alpha,4\alpha$- and $3\beta,4\beta$-dihydroxy- compounds of Formula I, wherein R is hydrogen, sodium, potassium, lower alkyl or Ph'-$C_nH_{2n}$ wherein $n$ is an integer from 1 to 4 and Ph' is phenyl, tolyl, anisyl, fluorophenyl or chlorophenyl, A is ethylene or cis-ethenylene, each of $R_1$ and $R_2$ are hydrogen or lower alkyl, and $R_3$ is lower alkyl, lower alkenyl or lower alkynyl, (3 to 6 ring-membered cycloalkyl)-$C_mH_{2m}$ or Ph'-$C_nH_{2n}$, wherein $m$ is an integer from 0 to 4, and $x$ is such from 0 to 2.

The highest degree of activity and stability is exhibited by compounds of Formula II

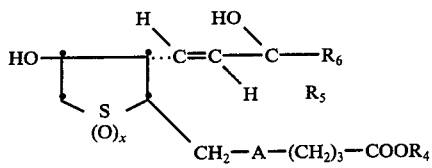

(II)

wherein $R_4$ is hydrogen, sodium, potassium or alkyl with up to 4 carbon atoms, A is ethylene or cis-ethenylene, $R_5$ is hydrogen or methyl and $R_6$ is n-(butyl, pentyl, hexyl, heptyl or octyl) or 2-methyl-2-n-(pentyl, hexyl or heptyl), 2-, 3- or 4-(cyclopropyl, cyclopentyl or phenyl)-ethyl, -propyl or -butyl and $x$ is 0–2.

Of said compounds of Formula II, it is advantageous to select those wherein $R_4$ is hydrogen, sodium or potassium, A is ethylene or cis-ethenylene, $R_5$ is hydorgen or methyl, $x$ is 0 to 2 and $R_6$ is n-pentyl, n-hexyl, 2-methyl-2-n-hexyl or 3-phenylpropyl, due to their outstanding activity and stability.

The compounds of the invention are prepared according to methods known per se, for example by:

a. reducing in a corresponding 7-[$3\alpha$-(3-oxo-3-hydrocarbylpropyl or 1-propen- or ynyl)-4-hydroxy-tetrahydro-$2\beta$-thienyl]-alkan- or 5-enoic acid, or a functional acid- or hydroxy-derivative, the sulfoxide or sulfone thereof, the oxo group to hydroxy, optionally accompained by introduction of a hydrocarbon radical, and hydrolyzing any resulting hydroxy derivative in basic or acidic media or any resulting acid amide or nitrile in strong basic media and, if desired, oxidizing resulting compounds with $x = 0$ to such with $x = 1$ or 2, or esterifying or salifying any resulting acid or hydrolyzing esters of salts, or hydrogenating any resulting dehydro derivative until the desired amount of hydrogen is consumed.

A functional acid derivative used in the above reactions is preferably a metal salt or an ester, e.g. such mentioned above for the compounds of Formula I, or advantageously the nitrile. A functional hydroxy derivative is either an ester or ether, such as a lower alkanoic acid ester, e.g. the acetate or propionate, but advantageously the 2-tetrahydropyranyl ether.

The reduction according to item a) is advantageously carried out either with simple or complex light metal hydrides, such as borohydrides or alkali metal or zince boron- or aluminum- hydrides or lower alkoxyhydrides, e.g. lithium aluminumhydride, sodium or zinc borohydride; lithium tri-t-butoxyaluminumhydride or triethoxyaluminumhydride; or according to Meerwein-PonndorfVerley with aluminum lower alkoxides, e.g. the ethoxide or advantageously the isopropoxide, preferably in the presence of a lower alkanol, e.g. isopropanol and/or a dihaloaluminum lower alkoxide, e.g. dichloroaluminum isopropoxide; or according to Grignard with an $R_2$- or $R_3$-metal compound, preferably and $R_{2,3}$-magnesium halide, e.g. the bromide or iodide; or $R_2$ or $R_3$ lithium.

Any resulting hydroxy or carboxy derivative is hydrolyzed in the usual manner, for example, a lower alkanoic acid ester of the 3-hydroxy compound, or the amide or nitrile or a lower alkyl ester of the heptanoic acid, with a base, such as an aqueous alkali metal hydroxide or carbonate, or an ether of the 3-hydroxy compound with an acid, such as a mineral, e.g. hydrohalic or sulfuric acid. Any resulting tetrahydrothiophene may be oxidized to the sulfoxide with conventional, mild oxidizing agents, such as alkali metall periodates, e.g. sodium periodate. The corresponding sulfones are obtained with stronger oxidation agents, such as hydrogen peroxide or aliphatic or aromatic peracids, e.g. peracetic or m-chloroperbenzoic acid. Any resulting acid may be esterified or salified in the usual manner, for example, with lower alkanols in the presence of mineral acids, preferably with lower diazoalkanes, or corresponding bases or ion exchangers, respectively. Any resulting dehydro derivative (e.g. A=ethenylene) can be selectively hydrogenated with rhodium catalysts or diimine. Said hydrogenation is preferably carried out prior to said hydrolysis of the 3-hydroxy derivatives, in order to protect the prop-1-enyl double bond.

Another process for the preparation of the compounds of the invention consists in:

b. oxidizong a corresponding 7-[$3\alpha$-(3-hydroxy-3-hydrocarbylpropyl or 1-propen- or ynyl)-4-hydroxy-tetrahydro-$2\beta$-thienyl]-alkanal or 5-alkenal, or a functional hydroxy-derivative, the sulfoxide or sulfone thereof, to the corresponding acid, and hydrolyzing any resulting hydroxy derivative in basic or acidic media and, if desired, oxidizing resulting compounds with $x = 0$ to such with $x = 1$ or 2, or esterifying or salifying any resulting acid, or hydrogenating any resulting dehydro derivative until the desired amount of hydrogen is consumed. A functional hydroxy derivative is either an ester or ether, such as a lower alkanoic acid ester, e.g. the acetate or propionate, but advantageously the 2-tetrahydropyranyl ether or the acetonide of the diol.

The oxidation according to item b) is carried out in the conventional manner for oxidizing aldehydes, or example, with catalytically activated or nascent oxygen respectively. The latter is derived from conventional oxidation agents, such as oxidizing acids or suitable salts or anhydrides thereof, e.g. periodic acid, sodium hypochlorite, chromic, ferric or cupric halides or sulfates, manganese IV, chromium VI, vanadium V, mercuric or silver oxide, in acidic or alkaline media. Said agents are used in the equivalent amounts and/or under careful conditions in order to prevent oxidations at other sites of the molecule. The resulting acids are, if desired or necessary, further reacted as shown under item a).

Another process for the preparation of the compounds of the invention consists in:

c. reacting the $2\beta$-(6-caboxyhexyl or 2-enyl)-4-hydroxy-tetrahydrothiophene-$3\alpha$-carboxaldehyde, or a functional acid- or hydroxy- derivative, the sufloxide or sulfone thereof, with the ylid of Formula III

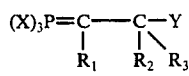 (III)

wherein X is lower alkyl or phenyl and Y is metallized or etherified hydroxy and hydrolyzing any resulting hydroxy derivative in basic or acidic media or any resulting acid amide or nitrile in strong basic media and, if desired, oxidizing resulting compounds with $x = 0$ to such wich $x = 1$ or 2, or esterifying or salifying any resulting acid or hydrolyzing esters or salts, or hydrogenating any resulting dehydro derivative until the desired amount of hydrogen is consumed.

A metallized compound III is preferably derived from an alkali metal, e.g. sodium or potassium, and in a corresponding ether Y is preferably tetrahydropyranyloxy or methoxymethoxy.

A functional acid derivative used in the above reactions is preferably a metal salt or an ester, e.g. such mentioned above for the compounds of Formula I, or advantageously the nitrile. A functional hydroxy derivative is either an ester or ether, such as a lower alkanoic acid ester, e.g. the acetate or propionate, but advantageously the 2-tetrahydropyranyl ether or said acetonide.

The reaction according to item c) is carried out according to the Wittig Reaction, i.e. either with the isolated reactant of Formula III, or the precursor thereof, e.g. by combining the corresponding phosphonium halide with a strong base, such as an alkali metal hydroxide, alkoxide, alkyl or phenyl compound first, then the aldehyde or ketone is added. Reaction c) is followed by acid hydrolysis in order to eliminate Y and the other conversions are carried out as shown under item a).

Another process for the preparation of the compounds of the invention consists in:

c'. reacting a corresponding [3α-(3-hydroxy-3-hydrocarbylpropyl or-1-propen- or ynyl)-4-hydroxy-tetrahydro-2β-thienyl]-acetaldehyde, or a functional hydroxy derivative, the sulfoxide or sulfone thereof, with the compound of Formula IV $$(X)_3P=CH-(CH_2)_3-Z \qquad (IV)$$

wherein X has the above meaning and Z is functionally converted carboxy and hydrolyzing any resulting hydroxy derivative in basic or acidic media or any resulting acid amide or nitrile in strong basic media and, if desired, oxidizing resulting compounds with $x = 0$ such with $x = 1$ or 2, or esterifying or salifying any resulting acid or hydrolyzing esters of salts, or hydrogenating any resulting dehydro derivative until the desired amount of hydrogen is consumed.

The reaction according to item c') is analogously carried out as that mentioned under item c) and the additional conversions as described under item a).

Also the functional derivatives, mentioned in this process, are those illustrated above under items a) to c).

The starting material used can be prepared according to the following formula schemes, which are illustrated in more detail by the examples herein:

 (IVa)

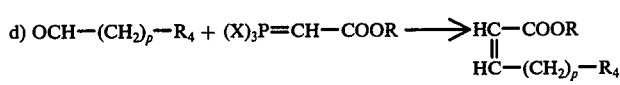 (V)

(VI)

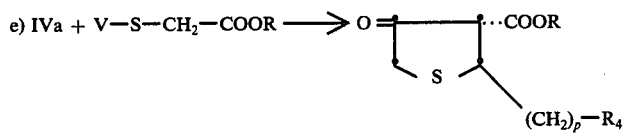 (VII)

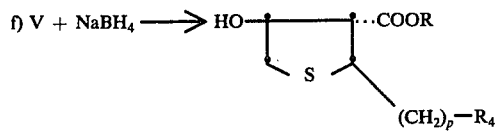 (VIII)

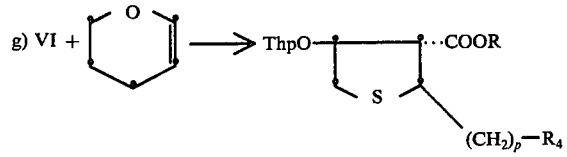

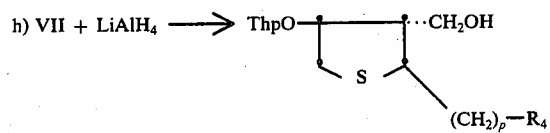 (IX)

i) VIII − H₂ ⟶ 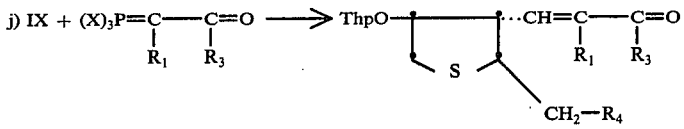

(X)

j) IX + (X)₃P=C(R₁)—C(R₃)=O ⟶ 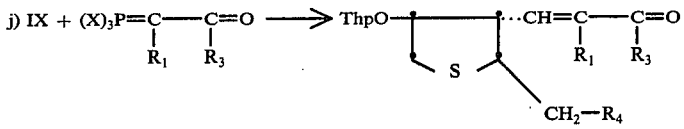

(XI)

k) IX + III —H⊕→ 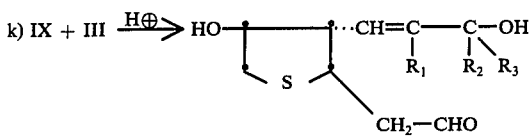

wherein R₄ is either A—(CH₂)₃—CN or a group capable of being converted into CHO, such as an etherified dihydroxymethyl (acetal) group, derived, for example, from lower alkanols or glycols, e.g. methanol, ethanol or ethylene glycol, V is hydrogen, an alkali metal or an ammonium radial derived from a tertiary base, e.g. a trialkylamine or pyridine, and p is the integer 0 or 1. Accordingly, in case R₄ is A—(CH₂)₃—CN, compounds of Formula X are starting materials for the reduction mentioned under item a), compounds of Formula IX are starting materials for c) and those of Formula XI such for d). In case R₄ in Formula X contains said group capable of being converted into CHO, and such compound is reduced as in a), whereupon CHO is liberated in acidic media, starting material for b) is obtained. Said products can be converted into the other starting materials as described above for the resulting compounds of Formula I. Another method for the preparation of the starting materials mentioned under item a) to d) is the following:

l) OCH—CH₂—R₄ + (X)₃P=CH—CHO ⟶ 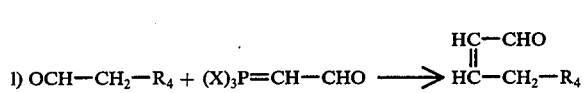 (XII)

m) XII + V—S—CH₂—R₅ ⟶ 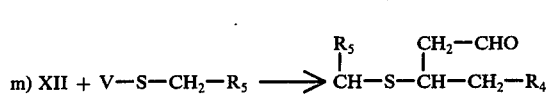 (XIII)

n) XIII + (X)₃P=C(R₁)—C(R₃)=O ⟶ 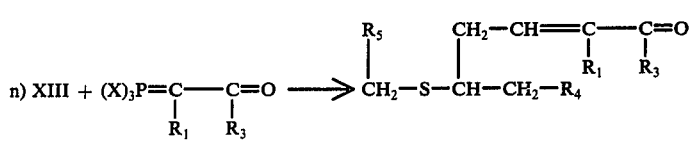 (XIV)

o) XIV + 2HO—(CH₂)₂—OH —H⊕→ 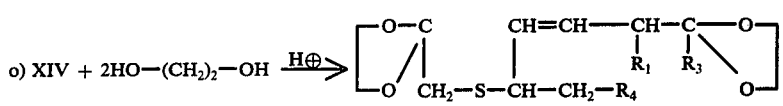 (XV)

p) XV + 2H₂O —H⊕→ 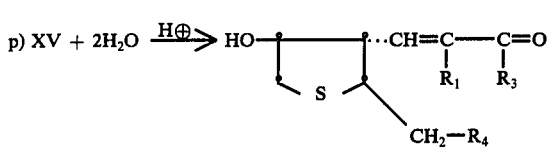 (XVI)

q) XIII + H₂O —1.H⊕ / 2.OH⊖→ 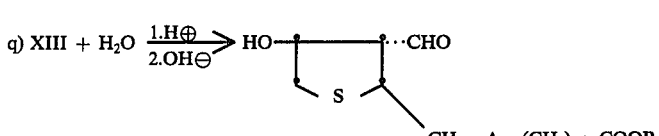 (XVII)

wherein R₅ is said group capable of being converted into CHO and the other symbols have the meanings given above. Accordingly, compounds of Formula XVI are starting materials for a) and XVII for c) if R₄ is A—(CH₂)₃—CN. In case R₄ in Formulae X and XVI is said group capable of being converted into CHO and such compound is analogously reduced as in a), whereupon CHO is liberated in acidic media, starting material for d) is obtained.

Another process for said starting material is depicted by the following scheme:

r) VIII $\begin{pmatrix} R_4 = CH(OC_2H_5)_2 \\ p = 0 \end{pmatrix}$ + R₃CWCl ⟶ 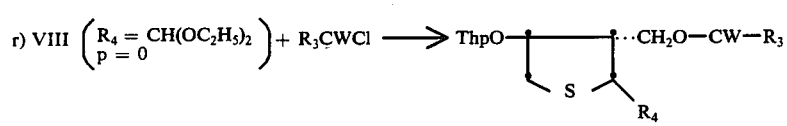 (XVIII)

s) XVIII $\xrightarrow{H\oplus}$ 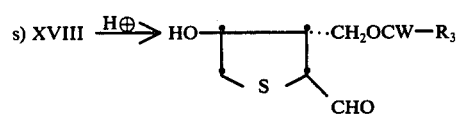 (XIX)

t) XIX + (C₆H₅)₃P=CHS—C₆H₅ ⟶ 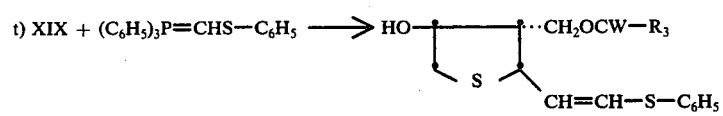 (XX)

u) XX + $\xrightarrow{OH\ominus}$ 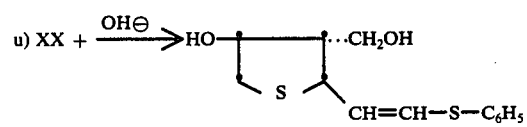 (XXI)

v) XXI + 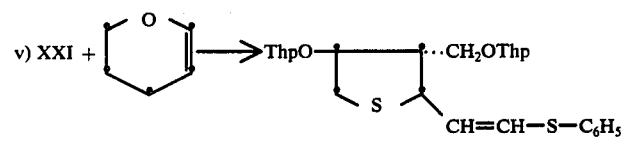 (XXII)

w) XXII + Ti— or Hg(II)-salts ⟶ 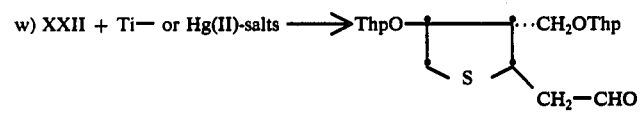 (XXIII)

x) XXIII + (X₃)P=CH—(CH₂)₃—Z ⟶ 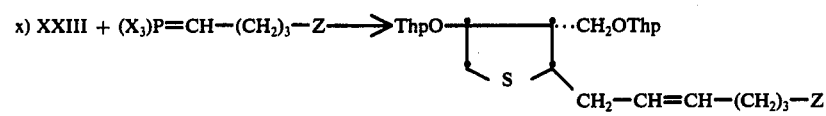 (XXIV)

y) XXIV $\xrightarrow{H\oplus}$ 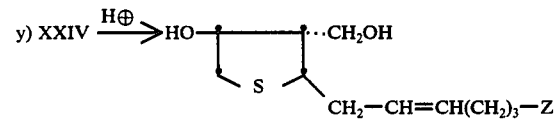 (XXV)

z) XXV + 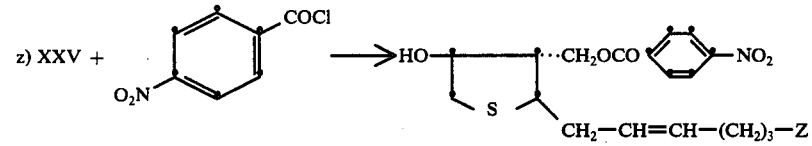 (XXVI)

za) XXVI + 1. 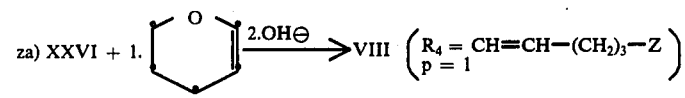 $\xrightarrow{2.OH\ominus}$ VIII $\begin{pmatrix} R_4 = CH=CH—(CH_2)_3—Z \\ p = 1 \end{pmatrix}$ zc) IX + 1. (C₆H₅)₃P=CBr₂ $\xrightarrow{2. C_4H_9Li}$ 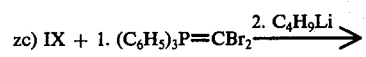 (XXVIII)

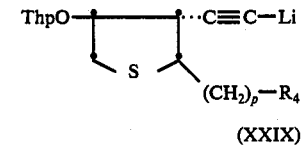 (XXIX)

wherein W is H₂ or O. The latter VIII is converted to the corresponding X as shown above.

Finally, selected compounds of the invention, or starting materials, can be prepared as follows:

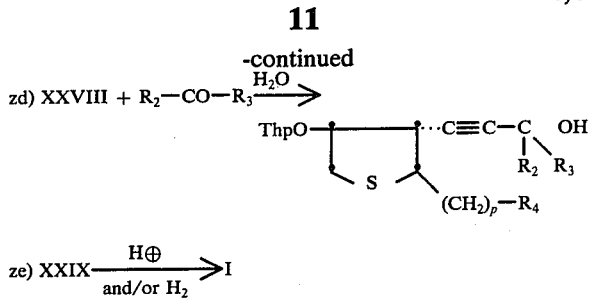

zd) XXVIII + $R_2$—CO—$R_3 \xrightarrow{H_2O}$ ze) XXIX $\xrightarrow[\text{and/or } H_2]{H^\oplus}$ I In variation to the above procedures for preparing the starting material, VI may be reduced directly to the diol corresponding to VIII ($R_4$=CH(OC$_2$H$_5$)$_2$ and $p$=0), which is esterified with benzoyl chloride to the di-benzoate and hydrolyzed to the 2-aldehyde. It is reduced with sodium borohydride, the resulting 2-carbinol reacted with PBr$_3$, the resulting bromide reacted with KCN and the diester hydrolyzed, to yield the compound of the Formula XXX, which is further processed thus:

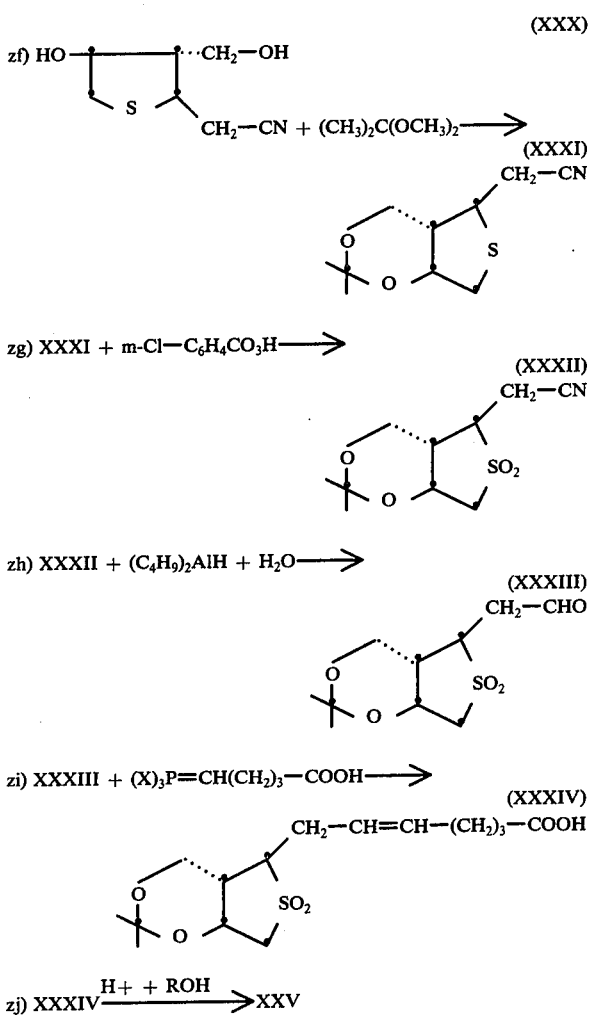

zf) (XXX)

(XXXI)

zg) XXXI + m-Cl—C$_6$H$_4$CO$_3$H ⟶ (XXXII)

zh) XXXII + (C$_4$H$_9$)$_2$AlH + H$_2$O ⟶ (XXXIII)

zi) XXXIII + (X)$_3$P=CH(CH$_2$)$_3$—COOH ⟶ (XXXIV)

zj) XXXIV $\xrightarrow{H+ \, + \, ROH}$ XXV and the latter compound further processed as shown above, to yield the 1,1-dioxides corresponding to XXVI, VIII, IX and X (r$_4$ is CH = CH—(CH$_2$)$_3$—COOR).

The above steps d), j), k), l), n), s), t), u), x), y) and zi) are carried out analogous to c) or d); the condensations according to e) or m) advantageously in di-lower alkyl-sulfoxides, e.g. dimethylsufloxide, followed by acid treatment; the reductions according to f), h) and zh) are performed analogously to a); the etherifications, ketalizations or trans-ketalizations according to g), o), v), z) or zf) respectively are advantageously carried out in the presence of an orgnic acid, e.g. picric or p-toluenesulfonic acid and an inert diluent, such as a halogenalkane, e.g. methylene chloride; the oxidation according to i) is performed according to b), preferably with the use of heavy mertal oxides, e.g. silver or chrominum VI oxide, advantageously in inert solvents, such as halogenalkanes and/or pyridine. The ring-closure according to p) occurs spontaneously after acid hydrolysis of the bisketal, whereas that according to q) requires first acid hydrolysis to convert R$_5$ to formyl and th following aldol condesnation occurs under basic conditions, e.g. in the pesence of alkali metals, their alkoxides or amides. The esterification or benzylation according to r) z) and zj) are carried out in the usual manner, either in the presence of a base, e.g. pyridine, or sodium hydride respectively, or of a acid, e.g. p-toluenesulfonic acid. Said intermediates, e.g. VIII, can also be oxidized to the sulfoxides or sulfones, as shown above for compounds I.

Resulting mixtures of isomers can be separated into the single isomers by methods in themselves known, e.g. by fractional distillation, crystallization and/or chromatography. Racemic products can likewise be resolved into the optical anitpodes, for example, by separation of diastereomeric esters or salts thereof, e.g. by the fractional crystallization of d- or l-2-pyrrolidone-3-carboxylates, -3β-acetoxy-Δ$^5$-etienates, -α-(2,4,5,7-tetranitro-9-fluorenylideneaminooxy)-propionates or α-methoxyphenylacetates, or salts of d- or l-α-phenethylamine, -1-phenyl-2-propylamine or -dihydrobietylamine.

The above reactions are carried out according to standard methods, in the presence or absence of diluents, preferably such as are inert to the reagents and are solvents thereof, of catalysts, condensing, neutralizing agents and/or inert atmospheres, at low temperatures, room temperature or elevated temperatures, at atmospheric or superatmospheric pressure. For example, any generated mineral or sulfonic acid may be neutralized with inorganic or organic bases, such as alkai or alkaline earth metal hydroxides, carbonates or bicarbonates or nitrogen bases, such as tri-lower alkylamines or pyridine.

The invention also comprises any modification of the above process, wherein a compound resulting as an intermediate at any stage thereof, is used as starting material and the remaining steps are carried out or the process is discontinued at any stage thereof, or in which the starting material is formed under the reaction conditions or is used in the form of its salts or other derivatives. In the above processes, those starting materials are advantageously selected, which yield the above-described preferred embodiments of the invention.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with:a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) adsorbents, colorants, flavors, sweeteners and coating agents, e.g. concentrated aqueous sugar solutions containing gum arabic, talcum and/or titanium dioxide, or solutions of laceqüers in easily volatile organic solvents, in order to obtain regular or sustained release formulations. Injectable compositions are preferably aqueous isotonic solutions or suspensions, and suppositiories are advantageously fatty emulsions or suspensions, e.g. in cocoa butter. They may be sterilized and/or contain adjuvants, such as preserving, stabilizing, wetting or emulsifying agents, solution promoters, salts for regulating the osmotic pressure and/or buffers. They may also contain other therapeutic agents. Said compositions are prepared according to conventional mixing, granulating or coating methods respectively and contain about 0.001 to 75%, preferably about 1 to 50% of the active ingredient.

The following examples are intended to illustrate the invention and are not to be construed as being limitations thereon. Temperatures are given in degrees Centrigrade, and all parts wherever gien are parts by weight. If not otherwise stated, all evaporations are carried out under reduced pressure, the infrared spectra are obtained from about 1-5% solutions in chloroform and the N.M.R. spectra from about 10% solutions in deuterochloroform at 60 Mc/sec. with tetramethylsilane as zero.

The base-equivalent mentioned for R is preferably derived from a therapeutically useful base, such as that of an alkali metal or alkaline earth metal, ammonium or a mono-, di- or tri-lower (alkyl or mono-, di- or trihydroxyalkyl)-ammonium, e.g. sodium or potassium; magnesium or calcium; mono-, di- or tri(methyl, ethyl or 2-hydroxyethyl)-ammonium or tris-(hydroxymethyl)-methylammonium.

EXAMPLE 1

To the solution of 53 mg of 7-[3a-(e-oxo-1-trans-octenyl)- 4β-hydroxy-tetrahydro-2β-thienyl]-heptanoic acid nitrile in 1ml of diethyl ether, 3ml of ethereal zinc borohydride prepared according to Gensler et al, J. Am. Chem. Soc. 82, 6074 (1960)]are added at once and the mixture is stirred at room temperature for two hours. Thereupon 0.1 ml of water are added, followed by 0.1 ml of glacial acetic acid and the mixture is stirred for 5minutes. It is diluted with 50 ml of diethyl ether, washed with saturated aqueous sodium chloride, dried and evaporated. The residue is subjected to preparative thin-layer chromatography on silica gel plates (1mm thick), eluted with ethyl acetate-methylene chloride (1:1) and of the two main fractions the slower moving isomer with Rf = 0.26 isolated, to yield the 7-[3α-(3β-hydroxy-1-trans-octenyl)-4β- hydroxy-tetrahydro-2β-thienyl]-heptanoic acid nitrile of the formula

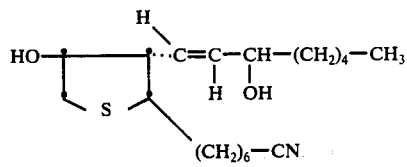

melting at 67°-69° after recrystallization from diethyl ether-n- hexane. The faster fraction with Rf=0.35 is the 3α-OH isomer.

The mixture of 69 mg thereof, 2 ml of methanol, 1 ml of water and 0.2 ml of 20% aqueous potassium hydroxide is heated in a sealed tube to 115°-120° for 72 hours and evaporated. The residue is taken up in 10 ml of water and 10 ml of saturated aqueous sodium chloride, the mixture neutralized with dry ice and extracted with diethyl ether. The extract is dried, evaporated and the residue recrystallized from diethyl ether, to yield the 7-[3α3α-(3β- hydroxy-1-trans-octenyl)-4β-hydroxy-tetrahydro-2β-thieny1-heptanoic acid melting at 88°-90°.

The 3α—OH isomer thereof is analogously prepared, Rf=0.36 on silica gel in ethyl acetate, benzene, cyclohexane, methanol, formic acid (20:20:5:5:0.2).

The starting material is prepared as follows: The mixture of 1.8 g of 9-cyano-2-nonenal, 1.4 g of 2,2-diethoxy-ethane- thiol and 50 μl of triethylamine is allowed to stand at room temperature for 48 hours. It is taken up in 100 ml of diethyl ether, the solution washed with water, dried and evaporated, to yield the 9-cyano-3-(2,2-diethoxy-ethylmercapto)-nonenal, showingin NMR spectrum peaks at 9.78, 4.55, 3.57 and 2.61 ppm.

To the solution of 2.6 thereof in 10 ml of diethyl ether, 3 g of 1-tri-n-butylphosphoranilidene-2-heptanone are added while stirring and the mixture is allowed to stand at room temperature overnight. It is evaporated, the residue subjected to preparative thin-layer chromatography on silica gel and twice eluted with ethyl acetate-methylene chloride (1:99), to yield the 16-cyano-10-(2,2-diethoxyethyl-mercapto)-8-hexadencene-6-one of the formula

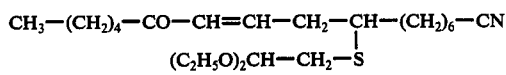

having an Rf = 0.33.

The mixture of 1.2 g thereof, 0.34 g of ethylene glycol, 30 mg of p-toluenesulfonic acid and 25 ml of benzene is refluxed for 15 hours on a water separator. After cooling it is diluted with 100 ml of diethyl ether, the solution washed with 10% aqueous potassium bicarbonate and water, dried and evaporated, to yield the bisethylene ketal of the 1-cyano-10-formylmethylmercapto-8- hexadecen-6-one showing in the NMR spectrum peaks at 5.4, 5.02, 3.93, 2.66 and 2.34 ppm.

The mixture of 1.15 g thereof, 30 ml of acetone and 0.19 g of p-toluenesulfonic acid is stirred for 40 hours at room temperature under nitrogen. It is evaporated at room temperature, the residue taken up in diethyl ether, the solution washed with 10% aqueous potassium carbonate and water, dried and evaporated. The residue is subjected to preparative thin-layer chromatography on silica gel, eluted three times with ethyl acetate-methylene chloride (9:1) and the two main fractions having Rf = 0.70 and 0.55 are isolated. The slower moving isomer (Rf = 0.55) is the desired 7-[3α-(3-oxo-1-trans-octenyl)-4β-hydroxy-tetrahydro-2β-thienyl]-heptanoic acid nitrile, showing in the mass spectrum fragments of 337, 319, 262, 220 and 209 m/e.

The faster moving isomer is the correponding 2β, 3α,4α-compound. It can be reduced, separated and hydrolized as shown above, to yield the 7-[3α-(3α-hydroxy-1-trans-octenyl)-4α-hydroxy-tetrahydro-2β-thienyl]-heptanoic acid of the formula

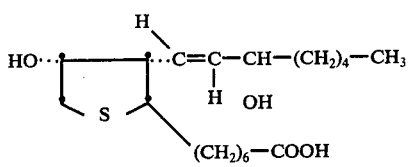

melting at 103°–104°. The 3β—OH isomer thereof has Rf=0.37 in the above acidic system.

EXAMPLE 2

The mixture of 58 mg of 7-[3α(3α-(3β-hydroxy-1-trans-octenyl)-4β-hydroxy-tetrahydro-2β-thienyl]-heptanoic acid, 3 ml of dioxane, 1 ml of water, 4 ml of methanol and 52 mg of sodium periodate is stirred at 0° for 24 hours and evaporated at room temperature. The residue is taken up in saturated aqueous sodium chloride, the mixture extracted four times with ethyl acetate-diethyl ether (1:1), the extract dried and evaporated. The residue is subjected to preparative thin-layer chromatography on silica gel and eluted with the less polar phase obtained from ethyl acetate-acetic acid- methanol-hexane-water (110:30:35:10:100), to yield the corresponding α- and β-sulfoxides of the formula

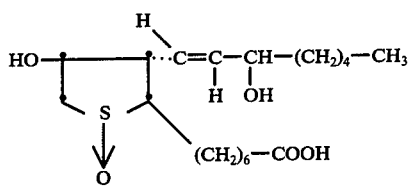

having Rf = 0.41 or m.p. 110°–125° and Rf = 0.50 or m.p. 110°–118° respectively.

In the analogous manner the 7-[1α and β-oxo-3α-(3α-hydroxy-1-trans-octenyl)-4α-hydroxy-tetrahydro-2β-thienyl]-heptanoic acids are obtained, having Rf = 0.38 or m.p. 105°–120° and Rf =0.49 or m.p. 96°–103° respectively.

EXAMPLE 3

To the solution of 45 mg of 7-[1,1-dioxo-3α(3-oxo-1-trans-octenyl)-4β-(2-tetrahydropyranyloxy)-tetrahydro-2β-thienyl]-heptanoic acid methyl ester in 3 ml of dioxane-methanol (1:1), 50 mg of sodium borohydride are added and the mixture stirred for half hour at room temperature. It is diluted with 20 ml of diethyl ether, washed with water and saturated aqueous sodium chloride, dried and evaporated. The residue is dissolved in 2ml of methanol and 50 μl of 2N sulfuric acid while stirring and the mixture is allowed to stand at room temperature overnight. It is diluted with 20 ml of diethyl ether, washed with water and saturated aqueous sodium chloride, dried and evaporated. The residue is subjected to preparative thin-layer chromatography on silica gel and eluted twice with ethyl acetate-methylene chloride (3:2), to yield the 7-[1,1-dioxo-3α-(3β-hydroxy-1-trans-octenyl)-4β-hydroxy-tetrahydro-2β-thienyl]-heptanoic acid methyl ester of the formula

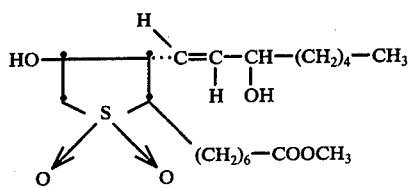

having Rf = 0.18 or m.p. 88°–90°.

The mixture of 48 mg thereof, 1 ml of methanol and 0.2 ml of 2N aqueous sodium hydroxide is allowed to stand at room temperature overnight and evaporated. The residue is taken up in 1 ml of water and 2 ml of saturated aqueous sodium chloride, the mixture acidified with 2N sulfuric acid and extracted with diethyl ether. The extract is washed with water and saturated aqueous sodium chloride, dried and evaporated, to yield the corresponding free acid melting at 87°–89°.

The starting material is prepared as follows: The mixture of 14 g of 7-cyanoheptanal, 38 g of ethyl triphenylphosphoranylidene-acetate and 100 ml of benzene is refluxed for 15 hours and evaporated. The residue is triturated with diethyl ether, filtered and the filtrate evaporated. The residue is allowed to stand overnight in the refrigerator, triturated with the minimum amount of diethyl ether, the suspension filtered, the filtrate evaporated, the residue distilled and the fraction boiling at 130°–138° /0.1 mm Hg collected, to yield the 9-cyano-2-nonenoic acid ethyl ester of the formula

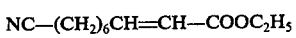

NC—(CH₂)₆CH=CH—COOC₂H₅

27.4 g thereof are added at once at 10° to the mixture prepared from 2.99 g of pulverized sodium, 125 ml of ethanol and 15.6 g of ethyl thioglycolate, evaporating the mixture after stirring it at room temperature and adding 100 ml of dimethylsulfoxide. The mixture is stirred at 10° for 1/2 hour and at room temperature for 2 hours, poured into 100 ml of cold 2N hydrochloric acid and extracted with diethyl ether. The extract is washed with water, dried and evaporated, to yield the 2-(6-cyanohexyl)-4-oxo-tetrahydrothiophen-3-carboxylic ,cid ethyl ester of the formula

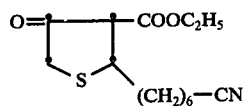

which is used as such without further purification.

To the solution of 24 g thereof in 240 ml of ethanol, 1.8 g of sodium borohydride are added during 5 minutes while stirring at 0°. After one-half hour, the mixture is poured onto ice water, extracted with diethyl ether, the extract washed with water and saturated aqueous sodium chloride, dried and evaporated. Each gram of the residue is chromatographed on 30 g of silica gel and the column eluted with ethyl acetate-methylene chloride (1:1), to yeild the 2-(6-cyanohexyl)-4-hydroxy-tetrahydrothiophen-3-carboxylic acid ethyl ester of the formula

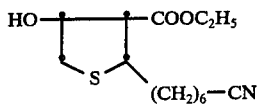

having the correct elemental analysis.

The mixture of 900 mg thereof, 538 mg of dihydropyrane, 45 mg of picric acid and 10 ml of methylene chloride is allowed to stand at room temperature overnight. It is evaporated, the residue taken up in diethyl ether, the solution washed three times with 10% aqueous potassium bicarbonate, once with water and saturated aqueous sodium chloride, dried and evaporated, to yield the 2-(6-cyanohexyl)-4-(2-tetrahydropyranyloxy)-tetrahydrothiophen-3-carboxylic acid ethyl ester of the formula

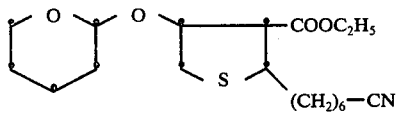

showing in the I.R. spectrum bands at 2931, 2855, 2254 and 1730 cm⁻¹.

To the solution of 5.015 g thereof in 200 ml of tetrahydrofuran, 900 mg of lithium aluminum hydride are added while stirring at −20°. After 3 hours, 200 ml of diethyl ether are added, followed by a few drops of methanol and water. It is filtered, the filtrate evaporated, the residue subjected to preparative thin-layer chromatography on silica gel and eluted twice with ethyl acetate-methylene chloride (1:9), to yield the 7-[3α-hydroxymethyl-4β-(2-tetrahydropyranyloxy)-tetrahydro-2β-thienyl]-heptanoic acid nitrile of the formula

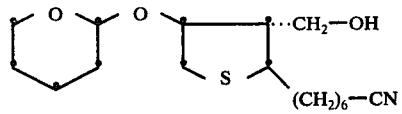

showing in the I.R. spectrum bands at 3500, 2930, 2855 and none at 1730 cm⁻¹.

The mixture of 1.3 g thereof, 10 ml of methanol, 5 ml of water and 2 ml of 20% aqueous potassium hydroxide is heated in a sealed tube to 115°–120° for 72 hours. It is evaporated, the residue taken up in 10 ml of water and 10 ml of saturated aqueous sodium chloride, the solution neutralized with dry ice and extracted with diethyl ether. The extract is dried, evaporated, the residue taken up in an excess of ethereal diazomethane and the solution evaporated after 1/2 hour, to yield the 7-[3α-hydroxymethyl-4β-(2-tetrahydropyranyloxy)-tetrahydro-2β-thienyl]-heptanoic acid methyl ester of the formula

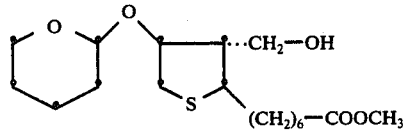

showing in the I.R. spectrum bands at 2930, 2855 and 1735 cm⁻¹.

To the solution of 1.2 g thereof in 60 ml of methylene chloride, 1.1 g of m-chloroperbenzoic acid are added while stirring at −15° and stirring is continued at room temperature for 48 hours. The mixture is neutralized with gaseous ammonia, filtered and evaporated, to yeild the 7-[1,1-dioxo-3α-hydroxymethyl-4β-(2-tetrahydropyranyloxy)-tetrahydro-2β-thienyl]-heptanoic acid methyl ester of the formula

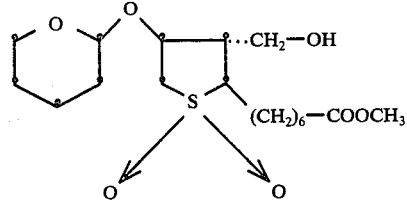

showing in the I.R. spectrum bands at 3455, 1720, 1100, 1060 and 1020 cm⁻¹.

To the solution of 400 mg thereof in 200 ml of methylene chloride, the solution of 1.6 g of pyridine-chromium trioxide complex are added at once and the mixture stirred at room temperature for 15 minutes. It is washed with water, dried, treated with charcoal, filtered and evaporated. The residue is taken up in 20 ml of diethyl ether, and 1.6 g of 1-tri-n-butylphosphoranylidene-2-heptanone are added while stirring and the mixture allowed to stand at room temperature overnight. It is evaporated, the residue subjected to preparative thin-layer chromatography on silica gel and eluted with ethyl acetate-methylene chloride (1:9) to yield the desired 7-[1,1-dioxo-3α-(3-oxo-1-trans-octenyl)-4β-(2-tetrahydropyranyloxy)-tetrahydro-2β-thienyl]-heptanoic acid methyl ester showing in the N.M.R. spectrum peaks at 6.92, 6.79, 6.59, 6.32, 4.72 and 3.55 ppm.

EXAMPLE 4

To the solution of 400 mg 7-[3α-(3-oxo-1-trans-octenyl)-4β-(2-tetrahydropyranyloxy)-tetrahydro-2β-thienyl]-heptanoic acid methyl ester in 20 ml of ethanol, 100 mg of sodium borohydride are added and the mixture stirred for half hour at 0°. It is diluted with 200 ml of diethyl ether, washed with water and saturated aqueous sodium chloride, dried and evaporated. The residue is dissolved in 20 ml of methanol, 10 mg of p-toluenesulfonic acid are added while stirring and the mixture is allowed to stand at room temperature overnight. It is diluted with 200 ml of diethyl ether, washed with water and saturated aqueous sodium chloride, dried and evaporated. The residue is subjected to preparative thin-layer chromatography on silica gel and eluted with ethyl acetate-methylene chloride(1:1), to yield the 7-[3α-(3β-hydroxy-1-trans-octenyl)-4β-hydroxy-tetrahydro-2β-thienyl]-heptanoic acid methyl ester of the formula

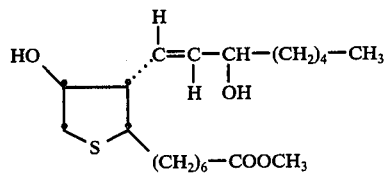

having an Rf = 0.302 and showing in the NMR spectrum bands at 5.5, 3.67, 2.28 and 0.90 ppm.

The mixture of 82 mg thereof, 10 ml of methanol and 1 ml of 0.1N aqueous sodium hydroxide is allowed to stand at room temperature overnight and evaporated. The residue is taken up in 10 ml of water and 10 ml of saturated aqueous sodium chloride, the mixture acidified with 0.1N hydrochloric acid and extracted with diethyl ether. The extract is washed with water and saturated aqueous sodium chloride, dried and evaporated, to yield the corresponding free acid, which is identical with the compound obtained according to Example I.

The starting material is prepared as follows: The solution of 1.1 g of 7-[3α-hydroxymethyl-4β-(2-tetrahydropyranyloxy)-tetrahydro-2β-thienyl]-heptanoic acid methyl ester in 5 ml of dry toluene is added dropwise to the mixture, prepared by adding 0.6 ml of dimethylsulfide to a solution of 0.8 g of N-chlorosuccimmide in 25 ml of toluene at 0°, while stirring at −25°. After two hours 0.84 ml of triethylamine are added, cooling is discontinued and after five minutes 20 ml of diethyl ether are added. The mixture is washed with water, 0.1N hydrochloric acid and saturated aqueous sodium chloride, dried and evaporated, to yield the 7-[3α-formyl-4β-(2-tetrahydropyranyloxy)-tetrahydro-2β-thienyl]-heptanoic acid methyl ester, having an Rf = 0.64 on silica gel plates eluted with ethyl acetate-methylene chloride(1:4).

The mixture of 1.1 g of 1-tri-n-butyl phosphoranylidene-2-heptanone and 20 ml of diethyl ether is stirred at room temperature overnight and evaporated. The residue is subjected to preparative thin-layer chromatography on silica gel plates(1 mm thick), eluted with ethyl acetate-methylene chloride (1:1) and the band corresponding to Rf = 0.534 yields the 7-[3α-(3-oxo-1-trans-octenyl)-4β-(2-tetrahydropyranyloxy)-tetrahydro-2β-thienyl]-heptanoic acid methyl ester.

EXAMPLE 5

To the solution of 200 mg of 7-[1,1-dioxo-3α-(3-oxo-1-trans-octenyl)-4β-(2-tetrahydropyranyloxy)-tetrahydro-2β-thienyl]-heptanoic acid methyl ester in 25 ml of tetrahydrofurane, cooled to −78°, 6 ml of 1-molar methylmagnesium iodide solution in diethyl ether are added dropwise while stirring. After one hour the mixture is diluted with wet diethyl ether, washed with water, dried and evaporated. The residue is dissolved in 8 ml of methanol, 40 mg of p-toluenesulfonic acid are added and the mixture is kept at 5° C overnight. It is neutralized with triethylamine, evaporated and the residue taken up in diethyl ether. The solution is washed with water, dried, evaporated and the residue crystalized from diethyl ether, to yield the 7-[1,1-dioxo-3α-(3β-hydroxy-3α-methyl-1-trans-octenyl]-4β-hydroxy-tetrahydro-2β-thienyl]-heptanoic acid methyl ester melting at 74.77°.

The mixture of 36 mg thereof, 0.5 ml of methanol and 50 μl of 20% aqueous potassium hydroxide is stirred at room temperature overnight and evaporated. The residue is dissolved in 4ml of water and 1 ml of saturated aqueous sodium chloride, then neutralized by adding dry-ice and extracted 6 times with diethyl ether. The combined extracts are washed with water, dried and evaporated to yield the 7-[1,1-dioxo-3α-(3β-hydroxy-3α-methyl-1-trans-oxtenyl)-4β-hydroxy-tetrahydro-2α-thienyl]-heptanoic acid of the formula

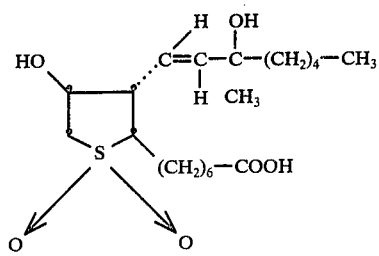

melting at 122°–123°.

EXAMPLE 6

To the solution of 400 mg of 7-[1,1-dioxo-3α-(3-oxo-1-trans-6-phenyl-hexenyl)-4β-(2-tetrahydropyranyloxy)-tetrahydro-2β-thienyl]-heptanoic acid methyl ester in 30 ml of ethanol, 87 mg of sodium borohydride are added and the mixture stirred for half hour at room temperature. It is diluted with 200 ml of diethyl ether, washed with water and saturated aqueous sodium chloride, dried and evaporated. The residue is dissolved in 20 ml of methanol, 10 mg of p-toluenesulfonic acid are added while stirring and the mixture is allowed to stand at room temperature overnight. It is diluted with 200 ml of diethyl ether, washed with water and saturated aqueous sodium chloride, dried and evaporated. The residue is subjected to preparative thin-layer chromatography on silica gel and eluted twice with ethyl acetate-methylene chloride (4:1), to yield the 7-[1,1-dioxo-3α-(3β-hydroxy-1-trans-6-phenylhexenyl)-4β-hydroxy-tetrahydro-2β-thienyl]-heptanoic acid methyl ester of the formula

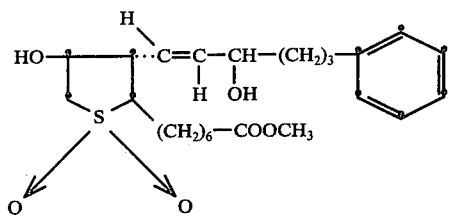

having Rf = 0.29 or m.p. 63°–65°.

The mixture of 148 mg thereof, 9 ml of methanol and 1.2 ml of 2N aqueous sodium hydroxide is allowed to stand at room temperature overnight and evaporated. The residue is taken up in 10 ml of water and 20 ml of saturated aqueous sodium cloride, the mixture acidified with 2N sulfuric acid and extracted with diethyl ether. The extract is washed with water and saturated aqueous sodium chloride, dried and evaporated, to yield the corresponding free acid melting at 122°–124°.

The starting material is prepared as follows: To the solution of 500 mg of 7-[1,1-dioxo-3α-hydroxymethyl-4β-(2-tetrahydropyranyloxy)-tetrahydro-2β-thienyl]-heptanoic acid methyl ester in 200 ml of methylene chloride, the solution of 2.01 g of pyridinechromium trioxide complex are added at once and the mixture stirred at room temperature for 15 minutes. It is washed with water, dried, treated with charcoal, filtered and evaporated. The residue is taken up in 20 ml of diethyl ether, and 725 mg of 1-tri-n-butylphosphoranylidene-5-phenyl-2-pentanone are added while stirring and the mixture allowed to stand at room temperature overnight. It is evaporated, the residue subjected to preparative thin-layer chromatography on silica gel and eluted with ethyl acetate-methylene chloride(35:65), to yield the 7-[1,1-dioxo-3α-(3-oxo-1-trans-6-phenyl-hexenyl)-4β-(2-tetrahydropyranyloxy)-tetrahydro-2β-thienyl]-heptanoic acid methyl ester showing in the NMR spectrum peaks at 7.22, 6.36, 6.1, 5.67, 1.58 and 1.38 ppm.

EXAMPLE 7

The solution of 100 mg of 7-[1,1-dioxo-3α-(3β-hydroxy-1-trans-octenyl)-4β-hydroxy-tetrahydro-2β-thienyl]-heptanoic acid in 5 ml of diethyl ether is treated with excess of ethereal diazomethane at 0° for one half hour and the solution evaporated under reduced pressure, to yield the corresponding methyl ester melting at 88° to 90° after recrystallization from ethyl acetate-methylene chloride(3:2).

In a similar manner the methyl esters of the acids illustrated by the previous examples are prepared.

EXAMPLE 8

50 mg of 7-[1,1-dioxo-3α-(3β-hydroxy-1-trans-octenyl)-4β-hydroxy-tetrahydro-2β-thienyl]-heptanoic acid are hydrogenated overnight in 10 ml of ethanol over 10 mg of tris-(triphenylphosphine)-rhodium (I) chloride at room temperature and atmospheric pressure. The catalyst is filtered off, the filtrate evaporated, the residue taken up in diethyl ehter and the solution decolorized with charcoal, to yield the 7-1,1-dioxo-3α-(3β-hydroxyoctyl)-4β-hydroxy-tetrahydro-2β-thienyl]-heptanoic acid of the formula

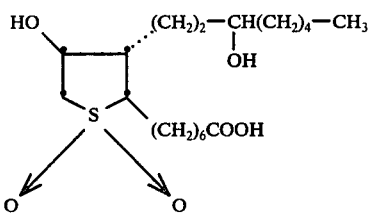

Analogously the unsaturated compounds of the remaining examples can be hydrogenated to the corresponding saturated compounds.

EXAMPLE 9

Analogous to the methods illustrated in the previous examples the following compounds of Formula II (wherein chain -3-OH is either α or β, and $R_5$ is β or α respectively), are prepared from equivalent amounts of the corresponding starting materials: A = $(CH_2)_2$, $R_5$ = H, X = 2:

| No. | 3-OH | $R_6$ | Rf or m.p. $R_4=CH_3$ | Rf or m.p. $R_4=H$ |
|---|---|---|---|---|
| 1 | α | $(CH_2)_5$—$CH_3$ | 0.375A (1:1) | 121–122° B |
| 2 | β | " | 0.22A (1:1) | 100–102° B |
| 3 | α | $(CH_2)_6$—$CH_3$ | 0.38A (1:1) | 123–125° C |
| 4 | β | " | 0.225A (1:1) | 114–116° C |
| 5 | α | $(CH_2)_7$—$CH_3$ | 0.359A (4:1) | 79–81° B |
| 6 | β | " | 0.250A (4:1) | 101–104° B |
| 7 | α | $(CH_2)_2$—$CH_3$ | 0.36A (13:7) | 0.23 E |
| 8 | β | " | 0.27A (13:7) | 0.17 E |
| 9 | α | $(CH_2)_3$—$CH_3$ | 0.44A (13:7) | 0.36 D |
| 10 | β | " | 0.30A (13:7) | 0.35 D |
| 11 | α | $C(CH_3)_2$—$(CH_2)_3$—$CH_3$ | 0.43A (13:7) | 90–95° B |
| 12 | β | " | 0.28A (13:7) | 102–103° B |
| 13 | α | $(CH_2)_2$—△ | 0.35A (13:7) | 83–87° B |
| 14 | β | " | 0.235A (13:7) | 0.44 D |

EXAMPLE 10

The mixture of 39 mg of 7-[1,1-dioxo-3α-(β-hydroxy-1-trans-octenyl)-4β-hydroxy-tetrahydro-2β-thienyl]-heptanoic acid (Example 3) and 5 ml of acetonitrile is heated to 60° while stirring and 20 μl of the solution of 121 mg of tris-(hydroxymethyl)-aminomethane in 0.2 ml of water are added dropwise. It is allowed to cool to room temperature while stirring and the precipitate formed collected, to yield the corresponding ammonium salt melting at 135° to 137°.

EXAMPLE 11

To the solution of 0.62 g of d-7-[1,1-dioxo- 3α-(3-oxo-1-trans-octenyl)-4β-(d-α-methoxy-phenylacetoxy)-tetrahydro-2β-thienyl]-heptanoic acid methyl ester in 5 ml of tetrahydropyran and 10 ml of methanol, 0.1 g of sodium borohydride are added at 0° while stirring. After stirring for 10 minutes at room temperature 1 ml of 10% aqueous potassium carbonate is added, stirring continued for 5 minutes and the mixture diluted with 10 ml of water. It is extracted with diethyl ether, the extract dried, evaporated, the residue subjected to preparative thin-layer chromatography on silica gel and eluted twice with ethyl acetate-methylene chloride (3:2), to yield as slower moving member the l-7-[1,1-dioxo-3α-(3β-hydroxy-1-trans-octenyl)-4β-hydroxy-tetrahydro-2β-thienyl]-heptanoic acid methyl ester having Rf=0.18, m.p. 47°–50° and $[\alpha]_{25}^D$ = −7.94° ± 0.25°.

The faster moving d-3β-hydroxy-isomer thereof has Rf = 0.31, m.p. 96°–99° and $[\alpha]_{25}^D$ = +13.94° ± 0.19°.

Said esters are hydrolyzed as previously described, to yield the corresponding acids:

3β— OH: m.p. 102°–103°; $[\alpha]_{25}^D$ −8.15°
3α— OH: m.p. 106°–108°; $[\alpha]_{25}^D$ = +6.85°

The starting material is prepared as follows: The mixture of 0.45 g of 7-[1,1-dioxo-3α-(3-oxo-1-trans-octenyl)-4β-(2-tetrahydropyranyloxy)-tetrahydro-2β-thienyl]-heptanoic acid methyl ester (Example 3), 10 ml of tetrahydrofurane, 3 ml of water and 0.1 ml of 2N hydrochloric acid is stirred at room temperature over night. It is diluted with 20 ml of diethyl ether, washed with water, dried and evaporated. The residue is preparatively chromatographed on silica gel and eluted with ethyl acetate-methylene chloride (1:4), to yield the corresponding free 4β-hydroxy compound having Rf=0.24.

To the solution of 0.13 g thereof in 1 ml of pyridine, 0.4 g of d-α-methoxy-phenylacetyl chloride are added dropwise at 0° while stirring, and stirring is continued for 5 hours at room temperature. The mixture is diluted with 20 ml of diethyl ether, washed with water, 0.5 N hydrochloric acid and again water, dried and evaporated. The residue is chromatographed on silica gel-plates (1mm thick) and eluted twice with ethyl acetate-methylene chloride (1:24), to yield as the slower moving fraction the d-7-[1,1-dioxo- 3α-(3-oxo-1-trans-octenyl)-4β-(d-α-methoxy-phenylacetoxy)-tetrahydro-2β-thienyl]-heptanoic acid methyl ester having Rf=0.213, m.p. 80°–81° (from diethyl ether) and $[\alpha]_{25}^D$ = +45.72° ± 0.19°.

The faster moving l-diastereomer with Rf=0.32, m.p. 63°–65° and $[\alpha]_{25}^D$ = 0.0° is analogously reduced and hydrolyzed, to yield the corresponding 3α and β-hydroxy-esters and -acids:

3α—OH ester: Rf=0.31; m.p. 96°–98°; $[\alpha]_{25}^D$ = 11.21 ± 0.18°
3α—OH acid: m.p. 110°–112° $[\alpha]_{25}^D$ = −9.05°
3β—OH ester: Rf=0.18; m.p. 42–48°; $[\alpha]_{25}^D$ = +10.71° ± 0.09°
3β—OH acid: m.p. 102°–103°; $[\alpha]_{25}^D$ = +7.3°

EXAMPLE 12

To the solution of 0.524 g of 7-[1,1-dioxo-3α-(3-oxo-4,4-dimethyl-1-trans-octenyl)-4β-(2-tetrahydropyranyloxy)-tetrahydro-2β-thienyl]-heptanoic acid methyl ester in 40 ml of tetrahydrofuran-ethanol (3:5), 0.116 g of sodium borohydride are added and the mixture stirred for half hour at room temperature. It is diluted with 300 ml of diethyl ether, washed with water and saturated aqueous sodium chloride, dried and evaporated. The residue is dissolved in 10 ml of methanol, 20 mg of p-toluenesulfonic acid are added and the mixture is allowed to stand at room temperature overnight. 50 ml of triethylamine are added, the mixture is evaporated under reduced pressure and the residue is extracted with diethyl ether. The extract is washed with water, dried and evaporated. The residue is subjected to preparative thin-layer chromotography on silica gel and eluted once with ethyl acetate-methylene chloride (13:7), to yield as the slower moving fraction the 7-[1,1-dioxo-3α-(3β-hydroxy-4,4-dimethyl-1-trans-octenyl)-4β-hydroxy-tetrahydro-2β-thienyl]-heptanoic acid methyl ester of the formula

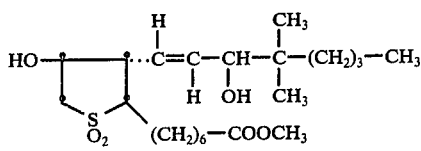

having Rf=0.28 and showing in the NMR spectrum bands at 0.88, 1.22, 1.36, 2.29, 3.68 and 5.61 ppm.

The mixture of 147 mg thereof, 3 ml of methanol and 1 ml of 1N aqueous sodium hydroxide is allowed to stand at room temperature overnight and evaporated. The residue is taken up in 5 ml of water and 5 ml of saturated aqueous sodium chloride, the mixture acidifed with 2N sulfuric acid and extracted with diethyl ether. The extract is washed with water and saturated aqueous sodium chloride, dried and evaporated, to yield the corresponding free acid which, on crystallization from methylene chloride-diethyl ether melts at 102°-103°.

The starting material is prepared as follows: To the solution of 5.9 g of 7-[1,1-dioxo-3α-hydroxymethyl-4β-(2-tetrahydropyranyloxy)-tetrahydro-2β-thienyl]-heptanoic acid methyl ester (Example 3) in 1lt. of methylene chloride, 24 g of pyridine-chromium trioxide complex are added at once and the mixture is stirred at room temperature for 15 minutes. It is washed with water, dried, treated with charcoal, filtered and evaporated. The residue is recrystallized from diethyl ether, to yield 7-[1,1-dioxo-3α-formyl-4β-(2-tetrahydro-pyranyloxy)-tetrahydro-2β-thienyl]-heptanoic acid methyl ester.

The mixture of 0.5 g thereof, 0.665 g of 1-tri-n-butyl-phosphoranylidene-3,3-dimethyl-2-heptanone and 20 ml of dimethyl ether is stirred at room temperature overnight. The crystalline material is filtered off, to yield the 7-[1,1-dioxo-3α-(3-oxo-4,4-dimethyl-1-trans-octenyl)-4β-(2-tetrahydro-pyranyloxy)-tetrahydro-2β-thienyl]-heptanoic acid methyl ester. The filtrates are evaporated and each gram of the residue is chromatographed on 30 g of silica gel and the column eluted with ethyl acetate-chloroform (1:9), to yield more of the same crystalline material obtained above. It melts after recrystallization from tetrahydrofuranediethyl ether at 106°-107°.

EXAMPLE 13

To the solution of 0.129 g of 7-[1,1-dioxo-3α(3β-hydroxy-4,4-dimethyl-1-trans-octenyl)-4β-hydroxy-tetrahydro-2β-thienyl]-heptanoic acid in 20 ml of acetonitrile, 0.3 ml of N aqueous sodium hydroxide are added dropwise at 60° while stirring vigorously. The mixture is allowed to cool slowly to room temperature, the fine white solid is filtered off and recrystallized from ethanol-ethyl acetate, to yield the corresponding sodium salt melting at 164°-167°.

Analogously the ammonium salt of said acid and tris-(hydroxymethyl)-aminomethane is prepared as a gummy material.

EXAMPLE 14

To the suspension of 5 g of (2-hydroxy-1-heptyl)-triphenyl-phosphonium iodide in 20 ml of dry tetrahydrofuran, 9.4 ml of 2.24 molar methyl lithium in diethyl ether are added over a period of two minutes while stirring under nitrogen. The mixture is cooled and maintained at −25°, for 30 minutes, cooled to −78° and the solution of 3.9 g of 7-[1,1-dioxo-3α-formyl-4β-(2-tetrahydropyranyloxy)-tetrahydro-2β-thienyl]-heptanoic acid methyl ester (Example 12) in 5 ml of tetrahydrofuran is added at once. After 5 minutes at −78° the mixture is warmed to 0° for 30 minutes and poured into water. It is extracted with diethyl ether, the extract dried and evaporated. The residue is dissolved in 15 ml of methanol, 50 mg of p-toluene sulfonic acid are added and the mixture is allowed to stand at room temperature overnight. 0.1 ml of triethylamine are added the mixture evaporated, the residue taken up in diethyl ether and the solution washed with water, dried and evaporated. The residue is subjected to preparative thin layer chromotography on silica gel and eluted twice with ethylacetate-methylene chloride (3:2), to yield the 7-[1,1-dioxo-3α-(3β-hydroxy-1-trans-octenyl)-4β-hydroxy-tetrahydro-2β-thienyl]heptanoic acid methyl ester, which is identical with that obtained according to Example 3.

EXAMPLE 15

The mixture of 0.36 g of 7-[1,1-dioxo-3α-(3β-hydroxy-4,4-dimethyl-1-trans-octenyl)-4β-hydroxy-tetrahydro-2-thienyl]-heptanal, 0.75 g of silver (II) oxide, 9 ml of tetrahydrofuran and 1 ml of water is stirred at room temperature for 24 hours. It is cooled to 0° and 10 ml of 2N sulfuric acid are added while stirring. After 10 minutes the solids are filtered off and washed 5 times with 5 ml of tetrahydrofuran each. The combined filtrate is extracted twice with 50 ml of diethyl ether, the extract washed throughly with water until neutral, dried and evaporated. The residue is dissolved in 1 ml of diethyl ether, seeded with 7-[1,1-dioxo-3α-(3β-hydroxy-4,4-dimethyl-1-trans-octenyl)-4β-hydroxytetrahydro-2β-thienyl]-heptonic acid and allowed to stand in the refrigerator overnight, to yield and compound identical with that obtained according to Example 12.

The starting material is prepared as follows: The mixture of 13.9 g of 7-cyanohepanal, 6.2 g of ethylene glycol, 100 ml of benzene and 50 mg of p-toluenesulfonic acid is refluxed for 2 hours on a water separator. It is washed with 10% aqueous potassium bicarbonate, dried, filtered and evaporated, to yield the 7-cyanoheptanal ethylene acetal, showing NMR-bands at 2.3, 3.85, 4.8 ppm.

The solution of 40 g thereof in 500 ml of benzene is cooled to 15° and 150 ml of 24.8% di-isobutylaluminum hydride in hexane are added dropwise while stirring under nitrogen and the temperature is kept below 20° C. Stirring is continued for 1/2 hour at 15°, the mixture further cooled to 0°, 20g of ice are added and stirring is continued 5 minutes. Thereupon 2N aqueous sulfuric acid is added dropwise to reach a pH=3 and the mixture is stirred at room temperature for one-half hour. The organic layer is separated, washed with 10% aqueous potassium bicarbonate and water, dried and evaporated. The residue is distilled and the fraction boiling at 105°/0.2 mm Hg collected, to yield the monoethylene acetal of the 1,8-octane dial.

The mixture of 25.7 g thereof, 45 g of triphenylphosphoranylidene-acetonitrile and 400 ml of benzene is refluxed for 15 hours and evaporated. The residue is triturated with diethyl ether, filtered and the filtrate evaporated. The residue is allowed to stand overnight in the refrigerator, triturated with the minimum amount of diethyl ether, the suspension filtered, the filtrate evaporated, the residue distilled and the fraction boiling at 139°–141°/0.1 mm Hg collected, to yield the 9-cyano-8-nonenal ethylene acetal.

10.51 g thereof are added at once at 10° to the stirred mixture, prepared from 1.15 g of pulverized sodium, 90 ml of ethanol and 6.16 g of ethyl thioglycolate and evaporating the mixture after stirring it at room temperature for 15 minutes. The residue is taken up in 15 ml of dimethylsulfoxide, the mixture stirred at 0° for one-half hour and at room temperature for two hours. It is poured into 100 ml of cold 2N hydrochloric acid an extracted with diethyl ether. The extract is washed with water, dried and evaporated, to yield the 7-(3-cyano-4-oxo-tetrahydro-2-thienyl)-heptanol ethylene acetal, showing in the IR-spectrum bands at 2250, 2221, 1743, 1732 cm$^{-1}$.

To the solution of 14.15 g thereof in 140 ml of ethanol, 0.95 mg of sodium borohydride are added during 5 minutes while stirring at $-6°$. After 15 minutes the mixture is poured into ice water, extracted with diethyl ether, the extract washed with water and saturated aqueous sodium chloride, dried and evaporated. Each gram of the residue is chromatographed on 30 g of silica gel and the column eluted with ethyl acetate-methylene chloride (1:2), to yield the 7-(3-cyano-4-hydroxy-tetrahydro-2-thienyl)-heptanol ethylene acetal showing NMR-bands at 1.65, 3.91, 4.86 ppm.

The mixture of 2.034 g thereof, 1.19 g of dihydropyrane, 0.1 g of picric acid and 50 ml of methylene chloride is allowed to stand at room temperature over night. It is diluted with 100 ml of diethyl ether, the solution washed three times with 10% aqueous potassium bicarbonate, once with water and saturated aqueous sodium chloride, dried and evaporated, to yield the 7-[3-cyano-4-(2-tetrahydropyranyloxy)-tetrahydro-2-thienyl)-heptanal ethylene acetal showing in the IR-spectrum bands at 2930, 2855, 2254 cm$^{-1}$.

To the mixture of 1.035 g thereof, 40 ml of benzene, 10 ml of diethyl ether, 2 ml of 24.8% diisobutylaluminum hydride in hexane are added dropwise while stirring at $-5°$ under nitrogen. After one hour 10 g of ice and 1 ml of acetic acid are added, the mixture is stirred at 0° for 15 minutes, the organic layer separated and washed with 10% aqueous potassium bicarbonate, water, dried and evaporated. Each gram of residue is chromatographed on 30 g of silica gel and the column eluted with ethyl acetate-methylene chloride (1:19), to yield the 7-(3-formyl-4-(2-tetrahydropyranyloxy)-tetrahydro-2-thienyl)-heptanal ethylene acetal showing in the IR spectrum bands at 2731, 1726, 1468, 1452 cm$^{-1}$.

The mixture of 0.8 g thereof, 1.02 g of 1-tri-n-butyl-phosphoranylidene-3,3-dimethyl-2-heptanone and 50 ml of diethyl ether is stirred under nitrogen at room temperature overnight and evaporated. Each gram of residue is chromotographed on 30 g of silica gel and the column is eluted with ethyl acetate-methylene chloride (1:19), to yield the 7-[3α-(3-oxo-4,4-dimethyl-1-transoctenyl)-4β-(2-tetrahydropyranyloxy)-tetrahydro-2β-thienyl]heptanal ethylene acetal showing NMR-bands at 0.86, 6.0, 6.26, 6.65 ppm.

The mixture of 490 mg thereof, 350 mg of m-chloroperbenzoic acid and 5 ml of methylene chloride is stirred at room temperature for 15 hours. The precipitate is filtered, the filtrate diluted with 20 ml of diethyl ether and washed with 10% aqueous sodium sulfite, water, 10% aqueous potassium bicarbonate and water, dried and evaporated, to yield the 7-[1,1-dioxo-3α-(3-oxo-4,4-dimethyl-1-trans-octenyl)-4β-(2-tetrahydropyranyloxy)-tetrahydro-2β-thienyl]-heptanal ethylene acetal showing NMR-bands at 0.86, 1.30, 1.57 ppm.

To the solution of 450 mg thereof in 20 ml of ethanol, 100 mg of sodium borohydride are added and the mixture stirred for half hour at 0°. It is diluted with 200 ml of diethyl ether, washed with water and saturated sodium chloride, dried and evaporated. The residue is dissolved in 50 ml of 60% aqueous acetic acid and the mixture stirred at room temperature for 24 hours. It is evaporated under reduced pressure, the residue triturated with diethyl ether, the solution washed with 10% aqueous potassium bicarbonate, dried and evaporated, to yield 7-[1,1-dioxo-3α-(3β-hydroxy-4,4-dimethyl-1-trans-octenyl)-4β-hydroxy-tetrahydro-2-thienyl]-heptanal showing NMR-bands at 0.9, 5.7, 9.8 ppm.

EXAMPLE 16

To the solution of 95 mg of 7-[1,1-dioxo-3α-(3-oxo-4,4-dimethyl-1-trans-octenyl)-4β-(2-tetrahydropyranyloxy)-tetrahydro-2β-thienyl]-5-cis-heptenoic acid methyl ester in 3 ml of tetrahydrofuran-ethanol (1:1) 50 mg of sodium borohydride are added and the mixture stirred for half hour at room temperature. It is diluted with 20 ml of diethyl ether, washed with water and saturated aqueous sodium chloride, dried and evaporated. The residue is dissolved in 2 ml of methanol and 50 ml of 2N sulfuric acid are added while stirring and the mixture is allowed to stand at room temperature over night. It is diluted with 20 ml of diethyl ether, washed with water and saturated aqueous sodium chloride, dried and evaporated. The residue is subjected to preparative thin-layer chromatography on silica gel and eluted twice with ethyl acetate-methylene chloride (3:2), to yield the 7-[1,1-dioxo-3α-(3β-hydroxy-4,4-dimethyl-1-trans-octenyl)-4β-hydroxy-tetrahydro-2β-thienyl]-5-cis-heptenoic acid methyl ester of the formula

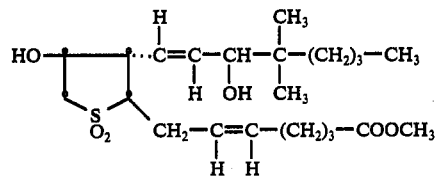

showing in the IR-spectrum bands at 2930, 2860 and 1725 cm$^{-1}$.

The mixture of 50 mg thereof, 1 ml of methanol and 0.2 ml of 2N aqueous sodium hydroxide is allowed to stand at room temperature overnight and evaporated. The residue is taken up in 1 ml of water and 2 ml of saturated aqueous sodium chloride, the mixture acidified with 2N sulfuric acid and extracted with diethyl ether. The extract is washed with water and saturated aqueous sodium chloride, dried and evaporated, to yield the corresponding free acid.

The starting material is prepared as follows: 8.65 g of ethyl 4,4-diethoxycrotonate are added at once at 0° to the mixture prepared from 1 g of pulverized sodium, 40 ml of ethanol and 4.94 ml of ethyl thioglycolate, evaporating the mixture after stirring it at room temperature and adding 43 ml of dimethylsulfoxide and 20 ml of dimethylformamide. The mixture is stirred at 0° for half hour and at room temperature for 2 hours, poored into cold water and extracted with diethyl ether. The aqueous layer is acidified with 21.7 ml of cold 2N hydrochloric acid and extracted with diethyl ether. The extract is dried and evaporated, to yield the ethyl 2-diethoxymethyl-4-oxo-tetrahydrothiophene-3-carboxylate showing in the IR spectrum-bands at 1750, 1725, 1660, 1615 cm$^{-1}$.

36.96 g thereof are added dropwise to a suspension of 5.1 g of sodium borohydride in 400 ml of ethanol, the mixture is cooled so that the temperature is kept below −60°. Stirring is continued for half hour, the mixture diluted with 1000 ml of diethyl ether, washed with cold water dried and evaporated, to yield the ethyl 2-diethoxymethyl-4-hydroxy-tetrahydrothiophene-3-carboxylate showing in the NMR spectrum bands at $\delta = 1.25$, 2.2 and 3.65.

TO the solution of 5 g thereof in 50 ml of tetrahydrofuran, cooled to 0°, 0.68 g of lithium aluminum hydride are added in portions over a 5 minute period. The mixture is stirred at 0° for half hour diluted with a few drops of water and 50 ml of diethyl ether and filtered. The filtrate is dried and evaporated, to yield the 2-diethoxymethyl-4-hydroxy-3-hydroxymethyl-tetrahydrothiophene showing in the IR spectrum-bands at 3610 and 3420 cm$^{-1}$.

The mixture of 0.995 g thereof, 4 ml of pyridine and 1.25 g of benzoyl chloride is stirred at 0° for 15 minutes and at room temperature for 4 hours. It is diluted with 2 ml of water, extracted with diethyl ether, the extract washed with water, N hydrochloric acid, 10% aqueous potassium carbonate, dried and evaporated, to yield the 4-benzoyloxy-3-benzoyloxymethyl-2-diethoxymethyl-tetrahydrothiophene showing in the NMR-spectrum bands at $\delta = 1.2$, 3.0, 3.65, 4.5, 7.4 and 8.1.

The mixture of 2.98 g thereof, 54 ml of acetic acid and 36 ml of water is heated to 60°-70° while stirring for 24 hours. It is evaporated, the residue extracted with diethyl ether, the extract washed with water and 10% potassium bicarbonate, dried and evaporated, to yield the 4-benzoyloxy-3-benzoyloxymethyl-2-carboxaldehyde showing in the NMR-spectrum bands at $\delta = 7.4$, 8.0 and 9.5.

To the solution of 119 mg thereof in 2 ml of ethanol, cooled at 0°, 38 mg of sodium borohydride are added at once and the mixture is stirred for half hour. It is extracted with diethyl ether, washed with water, dried and evaporated, to yield the 4-benzoyloxy-3-benzoyloxymethyl-2-hydroxymethyl-tetrahydrothiophene showing in the NMR-spectrum bands at $\delta = 3.7$, 4.1, 9.6, 7.4 and 8.0.

The mixture of 179 mg thereof, 25 ml of pyridine and 1 ml of toluene is added dropwise to that of 49 mg phosphorus tribromide, 3 ml of benzene and 1 ml of toluene, cooled to −5° while stirring. During the addition the temperature is kept below −3° and stirring is continued at −5° for 1 hour and at room temperature overnight. The mixture is extracted with diethyl ether, washed with water, dried and evaporated, to yield the 4-benzoyloxy-3-benzoyloxymethyl-2-bromomethyl-tetrahydrothiophene showing in the NMR-spectrum bands at $\delta = 3.7$, 4.6, 7.5 and 8.1

The mixture of 100 mg thereof, 2 ml of dimethylsulfoxide and 50 mg of potassium cyanide is stirred at room temperature overnight. It is extracted with diethyl ether, washed with water, dried and evaporated, to yield the α-(4-benzoyloxy-3-benzoyloxymethyl-tetrahydro-2-thienyl)-acetonitrile.

The mixture of 100 mg thereof, 2 ml of methanol and 0.5 ml of 10% aqueous potassium carbonate is stirred at room temperature for 1 hour. It is concentrated, the concentrate is extracted with diethyl ether, the extract dried and evaporated, to yield α-(4-hydroxy-3-hydroxymethyl-tetrahydro-2-thienyl)-acetonitrile.

The mixture of 100 mg thereof, 1 ml of 2,2-dimethoxypropane and 10 mg of p-toluenesulfonic acid is refluxed for 1 hour. 20μl of triethylamine are added and the mixture is evaporated. The residue is extracted with diethyl ether, the extract washed with water, dried and evaporated, to yield the acetonide of the α-(4-hydroxy-3-hydroxymethyl-tetrahydro-2-thienyl)-acetonitrile.

The mixture of 210 mg thereof, 175 mg of m-chloroperbenzoic acid and 5 ml of methylene chloride is stirred at room temperature for 24 hours. It is saturated with gaseous ammonia, diluted with 10 ml of diethyl ether, washed with water, 10% sodium bisulfite, water, dried and evaporated to yield the acetonide of the α-(4-hydroxy-3-hydroxymethyl-1,1-dioxo-tetrahydro-2-thienyl)acetonitrile.

To the solution of 240 mg thereof in 5 mg of benzene, cooled to 15°, 1 ml of a 1.9 molar solution of diisobutylaluminum hydride in hexane is added dropwise while stirring. Stirring is continued at 15°-20° for 2 hours, the mixture cooled to 0° and 0.5 ml of 2N sulfuric acid are added and stirring is continued at 0° for 15 minutes. The mixture is diluted with diethyl ether, washed with water, dried and evaporated, to yield and acetonide of the α-(4-hydroxy-3-hydroxymethyl-1,1-dioxo-tetrahydro-2-thienyl)-acetaldehyde.

The solution of 248 mg thereof in 5 ml of dimethylsulfoxide is added dropwise to the stirred solution, made from 665 mg of 4-carboxybutyl-triphenylphosphonium bromide in 10 ml of dimethyl sulfoxide by adding 2 ml of a 1.5 molar solution of sodium methylsulfinylmethide in dimethylsulfoxide, and stirring the mixture for 10 minutes at room temperature. It is poured into water, washed with diethyl ether, the aqueous layer acidified to pH=3 with 2N sulfuric acid and extracted with diethyl ether. The extract is washed with water, dried and evaporated, to yield the acetonide of the 7-(4-hydroxy-3-hydroxymethyl-1,1-dioxo-tetrahydro-2-thienyl)-5-cis-heptenoic acid.

The mixture of 200 mg thereof, 2 ml of methanol and 20 mg of p-toluenesulfonic acid is refluxed for 4 hours and evaporated. The residue is taken up in diethyl ether, the solution washed with water, dried and evaporated to yield the 7-(4-hydroxy-3-hydroxymethyl-1,1-dioxo-tetrahydro-2-thienyl)-5-cis-heptenoic acid methyl ester.

The solution of 290 mg thereof in 2 ml of pyridine is cooled to 0°, 185 mg of p-nitrobenzoylchloride are added and the mixture is stirred for 2 hours at 0° and 15 hours at room temperature. It is poured into water, extracted with diethyl ether, the extract washed with water, 2N sulfuric acid, water, dried and evaporated, to yield the 7-[4-hydroxy-3-(p-nitrobenzoyloxymethyl)-

1,1-dioxo-tetrahydro-2-thienyl]-5-cis-heptenoic acid methyl ester.

The mixture of 420 mg thereof, 5 ml of methylene chloride, 90 mg of dihydropyrane and 10 mg of picric acid is stirred at room temperature overnight. It is diluted with 20 ml of diethyl ether, washed with 10% aqueous bicarbonate, water, dried and evaporated, to yield the 7-[1,1-dioxo-3-(p-nitrobenzoyloxymethyl)-4-(2-tetrahydropyranyloxy)-tetrahydro-2-thienyl]-5-cis-heptenoic acid methyl ester.

The mixture of 500 mg thereof, 5 ml of methanol and 0.5 ml of 10% aqueous potassium carbonate is stirred at room temperature for 15 minutes. It is evaporated, the residue taken up in diethyl ether, the solution washed with water, dried and evaporated, to yield the 7-[1,1-dioxo-3-hydroxymethyl-4-(2-tetrahydropyranyloxy)-tetrahydro-2-thienyl]-5-cis-heptenoic acid methyl ester.

The the solution of 400 mg thereof in 200 ml of methylene chloride, 1.6 g of pyridine-chrominum trioxide complex are added at once and the mixture is stirred at room temperature for 15 minutes. It is washed with water, dried, treated with charcoal, filtered and evaporated. The residue is taken up in 20 ml of diethyl ether, and 1.7 g of 1-tri-n-butylphosphoranylidene-3,3-dimethyl-2-heptanone are added while stirring and the mixture is allowed stand at room temperature overnight. It is evaporated, the residue subjected to preparative thin-layer chromatography on silica gel and eluted with ethyl acetate-methylene chloride (1:9), to yield as the major fraction the 7-[1,1-dioxo-3α-(3-oxo-4,4-dimethyl-1-trans-octenyl)-4β-(2-tetrahydropyranyloxy)-tetrahydro-2β-thienyl]-5-cis-heptenoic acid methyl ester.

EXAMPLE 17

The solution of 0.5 g of α-[1,1-dioxo-3α-[4,4-dimethyl-3β-(2-tetrahydropyranyloxy)-1-trans-oxtenyl]-4β-(2-tetrahydropyranyloxy)-tetrahydro-2β-thienyl]-acetaldehyde in 5 ml of dimethylsulfoxide is added dropwise with stirring to the solution, made from 0.665 g of 4-carboxybutyl-triphenylphosphonium bromide in 10 ml of dimethylsulfoxide by adding 2 ml of a 1.5 molar solution of sodium methylsulfinylmethide in dimethylsulfoxide, and stirring the mixture for 10 min at room temperature. It is poured into water, washed with diethyl ether, the aqueous layer acidified to pH=3 with 2N sulfuric acid and extracted with diethyl ether. The extract is washed with water, dried and evaporated. The residue is dissolved in 5 ml of glacial acetic acid and 5 ml of water and the mixture is stirred at 45° C for 2 hours. It is evaporated, the residue taken up in diethyl ether, the solution washed with water, dried and evaporated, to yield the 7-[1,1-dioxo-3α-(3β-hydroxy-4,4-diemthyl-1-transoctenyl)-4β-hydroxy-tetrahydro-2β-thienyl]-5-cis-heptenoic acid, which is identical with that obtained according to Example 16.

The starting material is prepared as follows: To the mixture of 16.4 g of α-bromo-butyrolactone, 14.0 of mercaptoacetaldehyde diethylacetal and 100 ml of diethyl ether, the solution of 10 g of triethylamine in 100 ml of diethyl ether is added dropwise while stirring at room temperature. The stirring is continued over night, the mixture filtered and the filtrate evaporated. The residue is dissolved in diethyl ether, the solution washed with water, dried and evaporated to yield the α-(2-diethoxyethylmercapto)-butyrolactone showing in the NMR spectrum bands at 4.55, 2.68 and 1.1 ppm.

To the solution of 2.34 thereof in 20 ml of toluene, 10.6 ml of 1.4 molar diisopropylaluminum hydride in hexane are added dropwise at −70° under nitrogen while stirring. The mixture is stirred at −70° for two hours, 1.8 g of glacial acetic acid are added dropwise and the mixture is poured into water. It is extracted with diethyl ether, the extract washed with water, dried, and evaporated. Each gram of the residue is chromatographed on 30 g of silica gel and eluted with ethyl acetate-methylene chloride (1:1), to yield the 2-hydroxy-3-(2-diethoxyethylmercapto)-tetrahydrofuran, showing in the NMR-spectrum bands of 5.24, 4.55, 7.55 and 2.75 ppm.

The solution of 3.8 g thereof in 5 ml of dimethylsulfoxide is added at once to the solution made by adding 3.7 g of potassium t-butoxide to the stirred solution of 13.5 g of phenylmercaptomethyl-triphenylphosphonium chloride in 70 ml of dimethylsulfoxide and stirring the mixture under nitrogen and at room temperature for 10 min. The whole is stirred at room temperature overnight, poured into water and extracted with diethyl ether. The extract is washed with water, dried, evaporated and each gram of the residue chromatographed on 30 g of silica gel and eluted with ethyl acetate-methylene chloride (1:3), to yield the 3-(2-diethoxyethylmercapto)-5-phenylmercapto-4-pentenol, showing MNR-bands at 7.28, 6.25, 5.65 and 2.65 ppm.

To the solution of 300 mg thereof in 5 ml of pyridine, 0.5 ml of benzoyl chloride are added at once at 0° while stirring. The mixture is stirred at 0° for 2 hours, water is added and the whole is extracted with diethyl ether. The organic layer is washed with water, N hydrochloric acid, water, 10% aqueous potassium carbonate, again water, dried and evaporated, to yield the corresponding benzoate showing in the NMR-spectrum bands at 4.55, 3.6, 1.7 and 1.25 ppm.

The mixture of 300 mg thereof, 5 ml of glacial acetic acid and 3 ml of water is stirred at 50° for 20 hours. It is evaporated, the residue taken up in diethyl ether, the solution washed with water, dried and evaporated, to yield as an oily, amorphous residue the 2β-(2-benzoyloxyethyl)-4β-hydroxy-tetrahydrothiophene-3α-carboxaldehyde, showing in the NMR spectrum bands at 9.75, 8.0, 7.3 and 4.3 ppm.

The mixture of 100 mg thereof, 150 mg of 1-tri-n-butyl-phosphoranylidene-3,3-dimethyl-2-heptanone and 1 ml of diethyl ether is allowed to stand at room temperature overnight. It is evaporated, the residue is chromotographed on 5 g of silica gel and eluted with ethyl acetate-methylene chloride (1:9), to yield the 2β-(2-benzoyloxyethyl)-4β-hydroxy-3α-(4,4-dimethyl-3-oxo-1-trans-octenyl)-tetrahydrothiophene.

The mixture of 200 mg thereof, 5 ml of methylene chloride and 370 mg of m-chloroperbenzoic acid is stirred at 0° for 5 hours and at room temperature for 20 hours. It is diluted with diethyl ether, washed with 10% aqueous sodium bisulfite, 10% aqueous potassium bicarbonate, water, dried and evaporated, to yield the corresponding 1,1-dioxide.

To the solution of 215 mg thereof in 20 ml of diethyl ether 15 ml of ethereal zinc borohydride (shown in Example 1) are added at room temperature while stirring. Stirring is continued for two hours, whereupon 0.1 ml of water are added, followed by 0.5 ml of glacial acetic acid and the mixture is stirred for 5 minutes. It is diluted with 50 ml of diethyl ether, washed with saturated aqueous sodium chloride, dried and evaporated. The residue is subjected to preparative thin layer chromatography on silica gel and eluted with ethyl acetate-methylene chloride (13:7), and the slower moving fraction isolated, to yield the 2β-(2-benzoyloxyethyl)-4β-hydroxy-3α-(4,4-dimethyl-3β-hydroxy-1-trans-octenyl)-tetrahydrothiophene-1,1-dioxide.

The mixture of 220 mg thereof, 100 mg of dihydropyrane, 5 ml of methylene chloride and 10 mg of picric acid is stirred at room temperature overnight. It is evaporated, the residue taken up in 0.5 ml of 10% aqueous potassium carbonate and 5 ml of methanol, and the mixture is stirred at room temperature for two hours. It is diluted with 50 ml of diethyl ether, washed with water twice, dried and evaporated, to yield the 2β-(2-hydroxyethyl)-3α-[4,4-dimethyl-3β-(2-tetrahydropyranyloxy)-1-trans-octenyl]-4β-(2-tetrahydropyranyloxy)-tetrahydrothiophene-1,1-dioxide.

To the solution of 0.5 g thereof in 200 ml of methylene chloride, 1,6 g of pyridine-chromium trioxide complex are added at once and the mixture stirred at room temperature for 15 minutes. It is washed with water, dried, treated with charcoal, filtered and evaporated, to yield the α-[1,1-dioxo-3α-[4,4-dimethyl-3β-(2-tetrahydropyranyloxy)-1-trans-octenyl]-4β-(2-tetrahydropyranyloxy)-tetrahydro-2β-thienyl]-acetaldehyde.

EXAMPLE 18

The mixture of 200 mg of 7-[1,1-dioxo-3α-(3β-hydroxy-1-octynl)-4β-(2-tetrahydropyranyloxy)-tetrahydro-2β-thienyl]-heptanoic acid methyl ester, 10 ml of methanol and 10 mg of p-toluenesulfonic acid is allowed to stand at 5° overnight. Then 1 ml of 10% aqueous potassium carbonate is added, the mixture allowed to stand at room temperature for 20 hours, poured into 10 ml of water and 10 ml of saturated aqueous sodium chloride, the mixture is acidified with N hydrochloric acid to pH=3 and extracted with diethyl ether. The extract is washed with water, dried and evaporated, to yield the 7-[1,1-dioxo-3α-(3β-hydroxy-1-octynyl)-4β-hydroxy-tetrahydro-2β-thienyl]-heptanoic acid of the formula

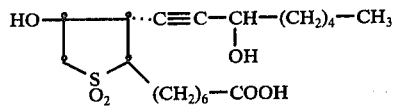

showing in the I.R.-spectrum bands at 2940, 2865 and 1710 cm$^{-1}$.

The starting material is prepared as follows: The solution of 400 mg of 7-[1,1-dioxo-3α-formyl-4β-(2-tetrahydropyranyloxy)-tetrahydro-2β-thienyl]-heptanoic acid methyl ester in 5 ml of dry methylne chloride is added dropwise to the solution made by adding of 1.3 g of triphenylphosphine, dissolved in 5 ml of methylene chloride, to the solution of 900 mg of tetrabromomethane in 50 ml of methylene chloride, cooled at 0°, and stirring the mixture for 2 minutes. The combined mixture is stirred at 0° C for 10 minutes and is washed with saturated aqueous sodium bicarbonate, dried and evaporated. The residue is triturated with diethyl ether, filtered and evaporated. The residue is dissolved in a small amount of diethyl ether, the solution allowed to stand in the refrigerator overnight, filtered and evaporated, to yield the 7-[1,1-dioxo-3α-(2,2-dibromovinyl)-4β-(2tetrahydropyranyloxy)-tetrahydro 2β-thienyl]-heptanoic acid methyl ester.

To the solution of 550 mg thereof 5 ml of dry tetrahydrofuran, cooled to −70° 1.3 ml of 1.6 molar n-butyl-lithium in hexane are added dropwise under nitrogen while stirring. After 2 hours stirring at −70° the mixture is poured into ice water and extracted with diethyl ether. The extract is dried and evaporated, to yield the 7-[1,1-dioxo-3α-ethinyl-4β-(2-tetrahydropyranyloxy)-tetrahydro-2β-thienyl]-heptanoic acid methyl ester.

To the solution 380 mg thereof in 5 ml of dry tetrahydrofuran, 0.7 ml of 1.6 molar n-butyl-lithium in hexane are added dropwise at −70° while stirring. After two minutes 110 mg of n-hexanal are added at once, stirring is continued at −70° for one-half hour, the mixture is poured into water and extracted with diethyl ether. The extract is washed with water dried and evaporated, to yield the 7-[1,1-dioxo-3α-(3β-hydroxy-1-octynyl)-4β-(2-tetrahydro pyranyloxy)-tetrahydro-2β-thienyl]-heptanoic acid methyl ester.

EXAMPLE 19

The solution of 380 mg of 7-[1,1-dioxo-3α-(3β-hydroxy-1-octynyl)-4β-hydroxy-tetrahydro-2β-thienyl]-heptanoic acid in 0.5 ml of tetrahydrofuran is added dropwise to that of 200 mg of sodium in 10 ml of liquid ammonia at −35°. The mixture is stirred at −30° for 1 hour, solid ammonium nitrate is added to destroy the excess of sodium and the mixture is poured into ice-water. It is acidified to pH=3 with 2N hydrochloric acid and extracted with diethyl ether. The extract is washed with water, dried and evaporated to yield the 7-[1,1-dioxo-3α-(3β-hydroxy-1-trans-octenyl)-4β-hydroxy-tetra hydro-2β-thienyl]-heptanoic acid, which is identical with that obtained according to Example 3.

EXAMPLE 20

Preparation of injection ampuls each containing 50 mg of the active ingredient:

| Formula: | |
|---|---|
| 7-[1,1-dioxo-3α-(3β-hydroxy-1-trans-octenyl)-4β-hydroxy-tetrahydro-2β-thienyl]-heptanoic acid | 170 g |
| 1,1,1-Trichloro-2-methyl-2-propanol | 85 g |
| Polysorbate 80 | 85 g |
| Methylcellulose 100 cps | 1,785 g |
| Sodium carboxymethylcellulose 70 MV | 51 g |
| Sodium chloride | 136 g |
| Water for injection | 17 lt. |

Procedure:

The chloropropanol is first dissolved in 13 lt of water at 90°, then the sodium carboxymethylcellulose is added while strirring, followed by the methylcellulose and stirring is continued for 15 minutes. The mixture is allowed to stand at 10° for 12 hours, combined with the polysorbate and the solution of the sodium chloride and active ingredient in 250 ml of water each. The resulting solution is made up to 17 lt with water, filtered through a sintered glass funnel, the filtrate palced into 2 lt sterilized bottles, steam-sterilized at 100° for 3.25 hours and filled into 5 ml ampuls with standard equipment.

This injectable solution (10$^{-2}$g/ml) can be used in the preparation of an infusion solution, by adding the proper amount thereof to infusion saline, to obtain a solution containing 10 μug of the active ingredient per ml (10$^{-5}$g/ml).

In the analogous manner injection- or infusion- solutions are prepared with the remaining compounds of the invention, especially those illustrated by the previous examples.

EXAMPLE 21

To the solution of 1.19 g of 7-[3α-(3-oxo-4,4-dimethyl-1-trans-octenyl)-4β-tetrahydropyranyloxy-tetrahydro-2β-thienyl]-5-cis-heptenoic acid nitrile in 10 ml of methanol, 80 mg of sodium borohydride are added in small portions at 0° while stirring for 15 minutes. The mixture is diluted with diethyl ether, washed with water, brine, dried and evaporated. The residue is dissolved in 20 ml of methanol, 12 ml of water and 6 ml of 20% aqueous potassium hydroxide and the mixture heated at 110° in a sealed tube for 48 hours. It is evaporated, the residue is dissolved in water, the solution neutralized with dry ice and extracted 5 times with diethyl ether. The extract is dried, evaporated and the residue treated with ethereal diazomethane at 0° C. The ether is removed, the residue dissolved in 10 ml of methylene chloride, the solution cooled at 0°, 340 mg of m-chloroperbenzoic acid are added and the mixture stirred at 0° for 4 hours. It is diluted with 50 ml of diethyl ether, washed with 1% aqueous sodium bisulfite, water, 10% aqueous potassium bicarbonate, water, dried and evaporated. The residue is dissolved in 10 ml of methanal, 10 mg of p-toluenesulfonic acid are added and the mixture stirred at room temperature over night. Two drops of triethylamine are added, the mixture evaporated, the residue subjected to preparative thin layer chromatography on silica gel and eluted once with ethyl acetate-methylene chloride (13:7), to yield the 7-[1,1-dioxo-3α-(3β-hydroxy-4,4-dimethyl-1-trans-octenyl)-4β-hydroxy-tetrahydro-2β-thienyl]-5-cis-heptenoic acid methyl ester with Rf=0.342, and the 7-[1,1-dioxo-3α-(3α-hydroxy-4,4-dimethyl-1-trans-octenyl)-4β-hydroxy-tetrahydro 2β-thienyl]-5-cis-heptenoic acid methyl ester with Rf=0.45.

The mixture of 400 mg of the former isomer 10 ml of methanol and 3 ml of N aqueous sodium hydroxide is stirred at room temperature over night and evaporated. The residue is dissolved in 10 ml of water, the solution treated with dry-ice, acidified with N hydrochloric acid and extracted 4 times with dimethyl ether, dried and evaporated, to yield the 7-[1,1-dioxo-3α- (3βhydroxy-4,4-dimethyl-1-trans-octenyl)-4β-hydroxy-tetrahydro-2β-thienyl]-5-cis-heptenoic acid melting at 55°-60°. In a similar manner the 3α-hydroxy-isomer yields the 7-[1,1-dioxo-3α-(3α-hydroxy-4,4-dimethyl-1-trans-octenyl-4β-hydroxy-tetrahydro-2β-thienyl]-5-cis-heptenoic acid melting at 84°-90°. Analogously the 7-[3α-(3-oxo-4,4-dimethyl-1-trans octenyl)-4α-tetrahydropyranyloxy-tetrahydro-2β-thienyl]-5cis-heptenoic nitrile yields the 7-[1,1-dioxo-3α-(3α and β-hydroxy-4,4-dimethyl-1-trans-oxtenyl-4α-hydroxy-tetrahydro-2β-thienyl]-5-cis-heptenoic acids having an Rf of 0.435 and 0.44 on silica gel eluted with benzene-dioxane acetic acid (20:20:1).

The starting material is prepared as follows: To the solution, made by adding dropwise 19 ml of n-butyl lithium in hexane to the solution of 3g of diisopropylamine in 100 ml of tetrahydro furan while stirring under nitrogen at −30° for 15 minutes and then cooling it to −70°, 7 g of carboethoxyethyl-(2,2-diethoxy)-ethylsulfide are added dropwise over a period of 4 minutes. After stirring at −70° for 1 hour, 7 g of 7-iodo-5-cis-heptenoic acid nitrile are added dropwise during 5 minutes. The mixture is stirred at −70° for 6 hours and allowed to warm up to room temperature overnight. It is poured into water, extracted with diethyl ether, the extract washed with water dried and evaporated. One gram of the residue is chromatographed on 30 g of silica gel and eluted with ethyl acetate-methylene chloride (1:19), to yield the ethyl 2-(2,2-diethoxyethylmercapto)-8-cyano-4-cis-octenoate showing NNR-bands at 5.8, 6.55 and 6.15 ppm.

To the solution of 5.4 g thereof in 150 ml of toluene, 15 ml of 1.4 molar diisopropylaluminum hydride in hexane is added during 15 minutes while stirring at −70° under nitrogen. After 2 hours, 4.2 g of glacial acetic acid are added, the mixture stirred for 15 minutes, poored into water and extracted twice with diethyl ether. The extract is washed with water, dried and evaporated, to yield the 2-)2,2-diethoxyethyl-mercapto)-8-cyano-4-cis-octenal showing NMR-bands at 5.4, 6.5 and 1.15 ppm.

The solution of 5 g thereof in 10 ml dimethyl sulfoxide is added at once to the solution made by adding 13.7 ml of 1.5 molar sodium methylsulfinylmethide in dimethyl sulfoxide, followed by 8.6 of phenylmercaptomethyl-triphenylphosphonium chloride in 80 ml of dimethyl-sulfoxide. The mixture is stirred under nitrogen at room temperature overnight, poured into water and extracted with diethyl ether. The extract is washed with water, dried, evaporated and each gram of the residue chromatographed on 30 g of silica gel and eluted with ethyl acetate-methylene chloride (1:24), to yield the 8-(2,2-diethoxyethylmercapto)-10-phenylmercapto-5,9-decadienoic acid nitrile showing NMR-bands at 7.4, 5.35 and 4.5 ppm.

The mixture of 1 g thereof, 200 ml of glacial acetic acid, 200 ml of water and 0.5 ml of trifluoroacetic acid is stirred at room temperature for 48 hours and is evaporated. The residue is taken up in diethyl ether, the solution washed with water, dried and evaporated, to yield the 7-(3α-formyl-4-hydroxy-tetrahydro-2β-thienyl)-5-cis-heptenoic acid nitrile showing NMR-bands at 5.4, 2.9 and 2.3 ppm.

The solution of 800 mg thereof in 5 ml of 1,2-dimethoxyethane is added at once to the solution, made by adding dropwise 1.35 g of 3,3-dimethyl-2-oxo-heptyl-dimethoxyphosphonate to the suspension of 0.228 g of 57% of sodium hydride in mineral oil and 50 ml of 1,2-dimethoxyethane, while stirring the mixture under nitrogen for one-half hour. The mixture is stirred at room temperature overnight, evaporated, the residue taken up in diethyl ether, the solution washed with water, dried, evaporated and each gram of the residue chromatographed on 30 g of silica gel and eluted with ethyl acetate-methylene chloride (1:9), to yield the 7-[3α-(3-oxo-4,4-dimethyl-1-trans-octenyl)-4-hydroxy-tetrahydro-2β-thienyl]5-cis-heptenoic acid nitrile, showing NMR-bands at 6.65, 5.45 and 2.3 ppm.

The mixture of 1.9 g thereof, 500 mg of dihydropyrane, 20 ml of methylene chloride and 20 mg of picric acid is stirred at room temperature overnight and evaporated. The residue is chromatographed on silica gel and eluted three times with ethyl acetate-hexane (1:4), to yield the 7-[3α-(3-oxo-4,4-dimethyl-1-trans-octenyl)-4β-tetrahydropyranyloxy-tetrahydro-2β-thienyl]-5-cis-heptenoic acid nitrile with Rf=0.368, and the 7-[3α-(3-oxo-4,4-dimethyl-1-trans-octenyl)-4α-tetrahydropyranyloxy-tetrahydro-2β-thienyl]-5-cis-heptenoic acid nitrile with Rf=0.332.

EXAMPLE 22

The solution of 1.28 g of 7-[3α-(3-oxo-4,4-dimethyl-1-trans-octenyl)-4β-benzoyloxy-tetrahydro-2β-thienyl)-heptanoic acid nitrile in 125 ml of diethyl ether is treated with an excess of ethereal zinc borohydride for one-half hour at room temperature, whereupon some water and acetic acid are added to destroy the excess of the hydride. The organic layer is separated, washed with water, dried, evaporated, and the residue dissolved in 10 ml of methanol, 6 ml of water and 3 ml of 20% aqueous potassium hydroxide. The mixture is heated in a sealed tube at 110° for 48 hours, evaporated and the residue taken up in water. The solution is treated with dry-ice, acidified with N hydrochloric acid and extracted 4 times with diethyl ether. The extract is washed with saturated aqueous sodium chloride, dried, evaporated and the residue treated with ethereal diazomethane. The ether is evaporated, the residue dissolved in 20 ml of methylene chloride and the solution treated at 0° C with 710 mg of m-chloroperbenzoic acid for three hours. The mixture is diluted with diethyl ether, washed with 1% aqueous sodium bisulfite, water, 10% aqueous potassium bicarbonate, water, dried and evaporated. The residue is subjected to preparative thinlayer chromatography on silica gel and eluted with ethyl acetate-methylene chloride (13:7), to yield the 7-[1,1-dioxo-3α-(3β-hydroxy-4,4-dimethyl-1-trans-octenyl)-4β-hydroxy-tetrahydro-2β-thienyl]-heptanoic acid methyl ester having Rf=0.28; it is identical with that obtained according to Example 12.

In a similar manner the 7-[3α-(3-oxo-4,4-dimethyl-1-trans-octenyl)-4α-benzoyloxy-tetrahydro-2β-thienyl]-heptanoic acid nitrile gives the 7-[1,1-dioxo-3α-(3β-hydroxy-4,4-dimethyl-1-trans-octenyl)-4α-hydroxy-tetrahydro-2β-thienyl]-heptanoic acid methyl ester with Rf=0.32 and its 3α-hydroxy isomer with Rf=0.45.

The mixture of 302 mg of the former isomer, 3 ml of methanol and 1 ml of N aqueous sodium hydroxide is stirred overnight and evaporated. The residue is taken up in water, the solution treated with dry-ice, acidified with N aqueous hydrochloric acid and extracted 4 times with diethyl ether. The extract is washed with water, dried and evaporated to yield 7-[1,1-dioxo-3α-(3β-hydroxy-4,4-dimethyl-1-trans-octenyl)-4β-hydroxy-tetrahydro-2β-thienyl]-heptanoic acid melting at 86–89°.

The starting material is prepared as follows: To the mixture of 13.6 g of methyl 2-bromo-8-cyano-octanoate, 11.6 g of 2,2-diethoxy-ethylmercaptan and 150 ml of methylene chloride, 5.56 g of triethylamine are added dropwise while stirring. After overnight-stirring-at room temperature the mixture is evaporated, the residue triturated with diethyl ether, washed with water, dried and evaporated, to yield the methyl 2-(2,2-diethoxyethylmercapto)-8-cyano-octanoate showing NMR bands at 4.58, 3.71 and 2.75 ppm.

To the stirred solution of 7.31 g thereof in 300 ml of toluene, 33 ml of 1.4 molar diisobutyl aluminum hydride in hexane are added dropwise during one-half hour at −70° under nitrogen and stirring is continued for 2.5 hours at −70°. 4.1 g of glacial acetic acid are added dropwise, the mixture is stirred for 15 minutes, poured into water and extracted twice with diethyl ether. The extract is washed with water and saturated aqueous sodium chloride, dried and evaporated, to yield the 2-(2,2-diethoxyethylmercapto)-8-cyano-octanal showing NMR-bands at 9.27, 4.5 and 2.3 ppm.

The solution of 6.68 g thereof in 70 ml of dimethylsulfoxide is added at once to the solution, made by adding 24 ml of 1.5 molar sodium methylsulfinylmethide in dimethyl sulfoxide to the stirred solution of 14 g of phenylmercaptomethyl-triphenylphosphonium chloride in 100 ml of dimethyl sulfoxide while stirring the mixture under nitrogen and at room temperature for 100 minutes. It is stirred at room temperature overnight, poured into water and extracted with diethyl ether. The extract is washed with water, dried, evaporated, each gram of the residue chromatographed on 30 g of silica gel and eluted with ethyl acetate-methylene chloride (4:96), to yield the 7-(2,2-diethoxyethylmercapto)-9-phenylmercapto 8-nonenoic acid nitrile showing NMR-bands at 6.41, 6.19, 5.78 and 1.3 ppm.

The mixture of 4.1 g thereof in 1 lt of glacial acetic acid, 1 lt of water and 2.5 ml of trifluoroacetic acid is stirred at room temperature for 48 hours and evaporated. The residue is taken up in diethyl ether, the solution washed with water, dried and evaporated. 2.26 g of the residue are added at once to the solution made by adding 4.65 g of 2-oxo-3,3-dimethylheptenyl dimethoxyphosphonate to the suspension of 783 mg of 57% of sodium hydride in mineral oil and 200 ml of 1,2-dimethoxyethane, while stirring the mixture at room temperature for one-half hour. It is stirred at room temperature overnight, evaporated, the residue triturated with diethyl ether, washed with water and saturated aqueous sodium chloride, dried, and evaporated. Each gram of the residue is chromatographed on 30 g of silica gel and eluted with ethyl acetate-methylene chloride (1:19), to yield the 7-[3α-(3-oxo-4,4-dimethyl-1-trans-octenyl)-4β-hydroxy-tetrahydro-2β-thienyl]heptanoic acid nitrile having Rf=0.19.

The mixture of 2.238 g thereof, 10 ml of pyridine and 960 mg of benzoyl chloride is stirred at room temperature for 2 hours. 10 ml of water are added, the mixture extracted with diethyl ether, the extract washed with water, N aqueous hydrochloric acid, water, 10% aqueous potassium bicarbonate, dried and evaporated. The residue is subjected to preparative thin-layer chromatography on silica gel and eluted twice with methylene chloride-ethyl acetate (19:1), to give the 7-[3β-(3-oxo-4,4-dimethyl-1-trans-octenyl)-4β-benzoyloxy-tetrahydro-2β-thienyl)-heptanoic acid nitrile having Rf=0.300, and the corresponding 4=-isomer having Rf=0.366.

EXAMPLE 23

According to the methods illustrated by the previous examples the following compounds of Formula I are prepared from equivalent amounts of the corresponding materials: A=cis-ethylene, R=R$_2$=H, R$_1$=trans-H, Rf on silica gel eluted with benzene-dioxane-ethyl acetate (20:20:1)

| No. | 4-OH | chain 3-OH | R$_3$ | x | Rf = |
|---|---|---|---|---|---|
| 1 | β | β | (CH$_2$)$_4$—CH$_3$ | 0 | 0.534 |
| 2 | β | α | " | 0 | 0.573 |
| 3 | α | α | " | 0 | 0.530 |
| 4 | α | β | " | 0 | 0.533 |
| 5 | β | β | " | 2 | 0.42 |
| 6 | β | α | " | 2 | 0.48 |
| 7 | α | α | " | 2 | 0.40 |
| 8 | α | β | " | 2 | 0.45 |
| 9 | β | β | CH(n-C$_4$H$_9$)$_2$ | 2 | 0.55, m.p. 78–80° |
| 10 | β | α | " | 2 | 0.605 |
| 11 | α | α | " | 2 | 0.525 |
| 12 | α | β | " | 2 | 0.565 |

EXAMPLE 24

Preparation of an inhalation-solution (mist) containing 0.3 mg/ml of the active ingredient:

| Formula: | |
|---|---|
| 7-[1,1-dioxo-3α-(3β-hydroxy-4,4-dimethyl-1-trans-octenyl)-4β-hydroxy-tetrahydro-2β-thienyl]-heptanoic acid | 0.300 g |
| 1,1,1-Trichloro-2-methyl-2-propanol | 3.000 g |
| Physiological saline | 1 lt |

Procedure:

The chloropropanol and active ingredient are dissolved each in 400 ml of the saline while stirring and heating on the water bath. Both solutions are combined, allowed to cool to room temperature, made up to one liter with saline, filtered through a sintered glass funnel, the filtrate steam-sterilized at 100° for 3½ hours and filled into 10 ml sterile nebulizerbottles.

EXAMPLE 25

To the solution of 420 mg of d-7-[1,1-dioxo-3α-(4,4-dimethyl-3-oxo-1-trans-octenyl)-4β-(d-α-methoxy-phenylacetoxy)-tetrahydro-2β-thienyl]-heptanoic acid methyl ester in 4 ml of tetrahydrofuran and 10 ml of diethyl ether, 7 ml of 0.145 Molar solution of zinc borohydride in ether are added at room temperature while stirring. After stirring for one-half hour at room temperature 0.5 ml of water and 0.5 ml of acetic acid are added and the mixture is stirred for additional 15 minutes. It is extracted with diethyl ether, the extract dried, evaporated, and the residue is taken in 10 ml of methanol. To the methanolic solution, 0.4 ml of 10% aqueous potassium carbonate are added while stirring. After stirring 15 minutes at room temperature the mixture is extracted with ether, the extract dried, evaporated and the residue subjected to preparative thin-layer chromatography on silica gel and eluted with ethyl acetate-methylene chloride (7:3) to yield the slower moving member $l$-7-[1,1-dioxo-3α-(4,4-dimethyl-3β-hydroxy-1-trans-octenyl)-4β-hydroxy-tetrahydro-2β-thienyl]-heptanoic acid methyl ester having Rf=0.306.

The faster moving d-3α-hydroxy-isomer thereof has Rf=0.45.

Said esters are hydrolized as previously described to yield the corresponding acids:

3β—-OH: m.p. 80°-84°; $[\alpha]_{25}^D$ = −12.70°/Yield 55%
3α—OH: m.p. 75°-85°; $[\alpha]_{25}^D$ = +24.25°/Yield 35%

The starting material is prepared as follows: The mixture of 23.6 g of 8-carbomethoxyoctanal, 12 g of morpholine and 150 ml of benzene is refluxed for one hour while removing the water with the use of a Dean-Stark apparatus. The benzene was removed by distillation under vacuum, the residue is disolved in 13 lit. of methylene chloride and the solution is cooled to −25°. To this mixture, a solution of 21.9 g of bromine and 100 ml of methylene chloride is added dropwise while stirring. After stirring at −25° for one-half hour the mixture is warmed up to −5°, 350 ml of water are added and the mixture is stirred for two hours. The organic layer is separated, dried and evaporated. The residue is disolved in 200 ml of methylene chloride, 30 g of mercaptoacetaldehyde diethyl acetal and 19 ml of triethyl amine are added and the mixture is stirred at room temperature for 20 hours. It is washed with water, dried and evaporated to give 2-(2,2-diethoxyethylmercapto-8-carbomethoxyoctanal showing NMR-bands at 9.15, 4.45 and 3.55 ppm.

The solution of 19.4 g thereof in 20 ml of tetrahydrofuran is added to the mixture made by adding dropwise at −60° 36 ml of 1.6 molar n-butyl lithium in hexane to the solution of 15.1 g of phenylthiomethyl-diethoxy phosphonate in 150 ml of tetrahydrofuran and stirring the mixture at −60° for 15 minutes. The mixture is warmed up to 0° and kept at this temperature for 24 hours. It is diluted with diethyl ether washed with water, dried and evaporated. The residue is chromatographed on silica gel using methylene chloride as eluant to give 8-(2,2-diethoxyethylmercapto)10-phenylmercapto-5,9-decadienoic acid methyl ester showing NMR-bands at 7.2, 5.35 and 4.5 ppm.

The mixture of 5.9 g thereof, 1 lit of glacial acetic acid, 700 ml of water and 2.5 ml of trifluoroacetic acid is stirred at room temperature for 72 hours and is evaporated. The residue is taken up in diethyl ether, the solution washed with water, dried and evaporated, to yield the 7-(3α-formyl-4-hydroxy-tetrahydro-2β-thienyl)-heptanoic acid methyl ester showing NMR-bands at 9.7, 2.8 and 1.4 ppm.

The solution of 10.8 g thereof in 50 ml of 1,2-dimethoxyethane is added at once to the solution, made by adding dropwise 19.7 g of 3,3-dimethyl-2-oxo-heptyl dimethoxyphosphonate to the suspension of 1.88 g of 50% of sodium hydride in mineral oil and 500 ml of 1,2-dimethoxy ethane while stirring the mixture under nitrogen for one-half hour. The mixture is stirred at room temperature for 2 hours, evaporated, the residue is taken up in diethyl ether, the solution washed with water, dried and evaporated and each gram of the residue chromatographed on 30 g of silica gel and eluted with ethyl acetate-methylene chloride (1:9) to yield the 7-[3α-(3-oxo-4,4-dimethyl-1-trans-octenyl)-4-hydroxy-tetrahydro-2β-thienyl] heptanoic acid methyl ester showing NMR-bands at 3.5, 2.2 and 1.2 ppm.

To the solution of 1 g thereof in 20 ml of methylene chloride, 1.5 gr of 85% m-chloroperbenzoic acid is added at once, at 0° with stirring. The mixture is stirred at 0° for 5 hours and then at room temperature for 15 hours. It is diluted with diethyl ether and washed with 10% aqueous sodium bisulfite water, 10% aqueous potassium bicarbonate, water, dried and evaporated to give 7-[1,1-dioxo-3α-(4,4-dimethyl-3-oxo-1-trans-octenyl)-4-hydroxytetrahydro-2β-thienyl]-heptanoic acid methyl ester showing NMR-bands at 6.58, 3.58 and 2.25 ppm.

The mixture of 1.1 gr thereof 250 mg of dihydropyrane, 30 mg of picric acid and 7 ml of methylene chloride is stirred at room temperature for 24 hours. The mixture is diluted with 20 ml of tetrahydrofuran-diethyl ether (1:3), washed with 10% aqueous potassium bicarbonate, water, dried and evaporated. The residue is recrystallized from diethyl ether-hexane to yield the 7-[1,1-dioxo-3α-(4,4-dimethyl-3-oxo-1-trans-octenyl)-4β-(2-tetrahydropyranyloxy)-tetrahydro-2β-thienyl]-heptanoic acid methyl ester having mp 102°-104° C.

The mixture of 280 mg thereof, 10 ml of methanol, 1 ml of tetrahydrofuran and 30 mg of p-toluenesulfonic acid is stirred at room temperature overnight. It is diluted with 20 ml of diethylether, washed with water, dried and evaporated to give the 4β-hydroxy compound having NMR-bands at 6.5, 3.5 and 1.2 ppm.

To the solution of 250 mg thereof in 5 ml of pyridine, 1 g of $d$-α-methoxy-phenylacetyl chloride are added dropwise at 0° while stirring, and stirring continued for 5 hours at room temperature. The mixture is treated with 1 ml of water, diluted with 20 ml of diethyl ether, washed with water, 0.5 N hydrochloric acid and again with water, dried and evaporated. The residue is chromatographed on silica gel plates (1 mm thick) and eluted with ethyl acetate-methylene chloride (9:1) to yield as the slower moving fraction the d-7-[1,1-dioxo-3α-(4,4-dimethyl-3-oxo-1-transoctenyl)-4β-(3-α-methoxy-phenylacetoxy)-tetrahydro-2β-thienyl]-heptanoic acid methyl ester having $R_f$=0.23, m.p. 59°–64° (from diethyl ether-hexane) and $[α]_{25}{}^D$= +34.42

The faster moving l-diastereoisomer with $R_f$=0.3 m.p. 99°–100° and $[α]_{25}{}^D$= −4.48 is analogously reduced and hydrolyzed to yield the corresponding 3α- and β-hydroxy acids:

3α-OH acid: m.p. 75°–80°; $[α]_{25}{}^D$= +14.26
3β-OH acid: $[α]_{25}{}^D$= −13.5°

EXAMPLE 26

To the solution of 4.98 of 7-[3α-(3-oxo-1-trans-decenyl)-4β-(o-chlorobenzoyloxy)-tetrahydro-2β-thienyl[-heptanoic acid nitrile in 200 ml of ether 76 ml of 0.011 Molar solution of zinc borohydride in ether is added dropwise and the mixture is stirred at room temperature for 1 hour. Water and glacial acetic acid are added dropwise, the organic layer is washed with water dried and evaporated. The residue is dissolved in 50 ml of methanol, 14.1 ml of 1 N aqueous sodium hydroxide are added and the mixture is stirred at room temperature for one hour and evaporated. The residue is extracted with diethyl ether, washed with water, dried and evaporated. Each gram of the residue is chromatographed from 50 g of silica gel using ethyl acetate-methylene chloride (7:3) as eluant to give the faster moving 7-[3α-(3α-hydroxy-1-transdecenyl)-4β-hydroxy-tetrahydro-2β-thienyl]-heptanoic acid nitrile showing IR-bands at 1050, 2245, 3400 and 3555 cm⁻¹ and the slower moving 7-[3α-(3β-hydroxy-1-trans-decenyl)-4β-hydroxy-tetrahydro-2β-thienyl]-heptanoic acid nitrile having m.p. 60° C.

Said nitriles are hydrolyzed as previously described to yield the corresponding acids:

3β-OH; m.p. 85°–87° C; yield 58%
3α-OH: m.p. 57°–59° C; yield 40%

The starting material is prepared as follows: 54 g of b 7-iodoheptanoic acid nitrile is added dropwise and with stirring at −60° to a solution made by adding dropwise and with stirring at −60°, 53.7 g of ethyl 2,2-diethoxyethylmercaptoacetate to a suspension of 9 g of sodium amide in 200 ml of ammonia and allowing the mixture to stir at −60° for 1 hour. The mixture is stirred at −60° for one hour and then allowed to warm up slowly to room temperature overnight. The mixture is diluted with 200 ml of water and extracted with diethyl ether. The extracts dried and evaporated and the residue is distilled under vacuum to give the 2-[2,2-diethoxy ethyl-mercapto]-8-cyano octanoic acid ethyl ester having boiling point 173°–176° C at 0.1 mm/Hg.

The mixture of 38 g thereof, 10 g of potassium hydroxide, 100 ml of water and 10 ml of ethanol is stirred at room temperature overnight. The miture is extracted with ether, the aqueous layer is treated with dry ice and acidified to pH=3 with 2 N aqueous hydrochloric acid and extracted with diethyl ether. The extract is dried and evaporated to give the 2-(2,2-diethoxy ethyl mercapto)-8-cyanooctanoic acid showing NMR-bands at 4.6, 2.3 and 1.19 ppm.

To the mixture of 25.3 g thereof 26.2 g of imidazole and 200 ml of tetrahydrofuran is added dropwise with stirring a solution of 11.5 g of thionyl chloride in 120 ml of tetrahydrofuran. The mixture is stirred for 15 minutes 120 ml of dry diethyl ether are added and filtered. The filtrates are evaporated under vacuum, the residue is taken in 400 ml of dry diethyl ether and decolorized with charcoal and filtered. The filtrate is added at once to a stirred suspension of 1.83 g of lithium aluminum hydride in 400 ml of diethyl ether at −50°. The stirring is continued for 1 hour while maintaining the temperature below 0° C. To the mixture, 25 ml of glacial acetic acid is added dropwise followed by 300 ml of water and the layers are separated. The ether layer is dried and evaporated and each gram of the residue is chromatographed from 5 gr of silica gel using methylene chloride as eluant to give 2-(2,2-diethoxy ethyl mercapto)-8-cyano-octanol, which was converted to 7-(2,2-diethoxy ethyl mercapto)-9-phenylmercapto-8-nonenoic acid nitrile, as previously described in example 22.

The mixture of 8.9 g thereof 900 ml of glacial acetic acid, 350 ml of water and 9.5 ml of trifluoro acetic acid is stirred at room temperature for 72 hours and evaporated. The residue is dissolved in diethyl ether, washed with water, 10% aqueous potassium bicarbonate dried and evaporated. The residue is added to a mixture made by adding dropwise 10.1 g of 2-oxo-nonyldimethoxyphosphonate to a suspension of 1.9 g of 50% sodium hydride in mineral oil and stirring the mixture at room temperature for one-half hours. The mixture is stirred at room temperature for one hour and evaporated. The residue is extracted with ether, washed with water, dried and evaporated. Each gram of the residue is chromatographed from 30 grams of silica gel using ethyl acetate-methylene chloride (1:9) as eluant to give 7-[3α-(3-oxo-1-trans-decenyl)-4-hydroxytetrahydro-2β-thienyl]-heptanoic acid nitrile showing NMR-bands at 2.4, 1.4 and 0.9 ppm.

To the solution of 3.87 g thereof in 15 ml of pyridine 2.12 g of o-chloro benzoyl chloride is added dropwise with stirring at 0°. The mixture is stirred at room temperature for two hours, water is added and extracted with diethyl ether. The extract is washed with water 2N aqueous hydrochloric acid, again with water dried and evaporated. Each gram of the residue is chromatographed from 50 g of silica gel using ethyl acetate methylene chloride (5:95) as eluant to give the faster moving 7-[3α-(3-oxo-1-trans-decenyl)-4α-(o-chlorobenzoyloxy)-tetrahydro-2β-thienyl]-heptanoic acid nitrile, showing NMR bands at 7.35, 5.4 and 1.25 ppm and the slower moving 7-[3α-(3-oxo-1-trans-decenyl)-4β-(o-chlorobenzoyloxy)-tetrahydro-2β-thienyl]-heptanoic acid nitrile showing NMR-bands at 7.0, 5.5 and 0.85 ppm.

EXAMPLE 27

To the solution of 350 g of 7-[3α-(3β-hydroxy-1-transoctenyl)-4β-hydroxy-tetrahydro-2β-thienyl-heptanoic acid in 10 ml of dry methylene chloride 260 mg of m-chloroperbenzoic acid are added at 0° with stirring. The stirring is continued at 0° for 2 hours, the mixture is diluted with diethyl ether washed with 10% aqueous sodium bisulfite, water, dried and evaporated. The residue is chromatographed on 10 g of silica gel using ethyl acetate methylene chloride (4:1) as eluent and gives the corresponding 1,1-dioxo-2β-thienyl heptanoic acid described in Example 3 (yield 85%).

EXAMPLE 28

To the solution of 370 mg of 7-[1-oxo-3α-(3β-hydroxy-1-trans-octenyl)-4β-hydroxy-tetrahydro-2β-thienyl]-heptanoic acid in 10 ml of dry methylene chloride 175 mg of m-chloroperbenzoic acid are added at 0° with stirring. The stirring is continued for 3 hours at 0°. The mixture is diluted with diethyl ether and washed with 10% aqueous sodium bisulfite, water, dried and evaporated. The residue is chromotagraphed from 10 g of silica gel using ethyl acetate: methylene chloride (4:1) as eluant and corresponding acid described in Example 3, yield 90%.

EXAMPLE 29

According to the methods illustrated by the previous examples the following compounds of Formula I are prepared from equivalent amounts of the corresponding starting materials $R=R_1=R_2=H$:

EXAMPLE 31

The mixture of 1.02 g of 7-[1,1-dioxo-3α-(3β-hydroxy-4,4-dimethyl-1-trans-octenyl)-4β-hydroxy-tetrahydro-2β-thienyl]-heptanoic acid methyl ester, 596 mg of dihydropyrane, 50 mg of picric acid and 50 ml of methylene chloride is stirred at room temperature overnight. It is washed with 10% aqueous potassium bicarbonate, water, dried and evaporated. The residue is dissolved in methanol and the solution heated with 5 ml of N aqueous sodium hydroxide. After stirring over-

| No. | 4-OH | Chain 3-OH | A | $R_3$ | x | Rf = m.p. | Yield % |
|---|---|---|---|---|---|---|---|
| 1 | β | β | $CH_2CH_2$ | $(CH_2)_6CH_3$ | 0 | $r_f = .558$ | 55 |
| 2 | β | α | " | " | 0 | $r_f = .590$ | 35 |
| 3 | α | α | " | " | 0 | $r_f = .539$ 85–87° C | 51 |
| 4 | α | β | " | " | 0 | $r_f = .557$ 57–59° C | 45 |
| 5 | β | β | " | $\begin{array}{c}CH_3\\|\\C-(CH_2)_3CH_3\\|\\CH_3\end{array}$ | 0 | $r_f = .612$ | 58 |
| 6 | β | α | " | " | 0 | $r_f = .643$ | 30 |
| 7 | α | α | " | " | 0 | 0.551 | 52 |
| 8 | α | β | " | " | 0 | 0.585 | 45 |
| 9 | β | β | " | $CH_2CH_2-\langle O\rangle$ | 0 | 0.526 | 50 |
| 10 | β | α | " | " | 0 | 0.538 | 30 |
| 11 | α | β | " | " | 0 | 0.519 | 49 |
| 12 | α | α | " | " | 0 | 0.488 | 28 |
| 13 | β | β | Cis-CH=CH | $(CH_2)_6CH_3$ | 0 | 0.53 | 55 |
| 14 | β | α | " | " | 0 | 0.55 | 35 |
| 15 | α | α | " | " | 0 | 0.543 | 45 |
| 16 | α | β | " | " | 0 | 0.583 | 35 |
| 17 | β | β | " | " | 2 | 73–76° | 25 |
| 18 | β | β | " | $\begin{array}{c}CH_3\\|\\C-(CH_2)_3CH_3\\|\\CH_3\end{array}$ | 0 | 0.567 | 56 |
| 19 | β | α | " | " | 0 | 0.601 | 35 |
| 20 | α | α | " | " | 0 | 0.581 | 49 |
| 21 | α | β | " | " | 0 | 0.608 | 30 |
| 22 | β | β | $CH_2$ | " | 2 | 0.489 | |
| 23 | β | α | " | " | 2 | 0.550 | |
| 24 | α | α | " | " | 2 | 0.460 | |
| 25 | β | β | " | " | 2 | 0.545 | |
| 26 | β | β | $(CH_2)_2$ | $CH[(CH_2)_3CH_3]_2$ | 2 | 0.437 | |
| 27 | β | α | " | " | 2 | 0.500 | |
| 28 | α | α | " | " | 2 | 0.585 | |
| 29 | α | β | " | " | 2 | 0.690 | |
| 30 | α | α | " | $n-C_5H_{13}$ | 2 | 0.416 | |

Rf's are measured on silica gel plates eluted with benzene-dioxane acetic acid (2:2:0.1).

EXAMPLE 30

The solution of 200 mg of 7-[1,1-dioxo-3α-(3β-hydroxy-4,4-dimethyl-1-trans-octenyl)-4β-hydroxy-tetrahydro-2β-thienyl]-heptanoic acid methyl ester in 10 ml of ethanol is hydrogenated over 30 mg of 5% palladium on charcoal at room temperature and atmospheric pressure. The catalyst is filtered off and the filtrate evaporated. The residue is dissolved in 10 ml of methanol and heated overnight at room temperature with 2 ml of N aqueous sodium hydroxide. The mixture is evaporated, the residue dissolved in 10 ml of water and the solution acidified with N hydrochloric acid. It is extracted with diethyl ether, the extract dried and evaporated, to yield the 1,2-dihydro-derivative of said compound having $R_f=0.540$ on silica gel eluted with benzene-dioxane-acetic acid (2:2:0.1).

The similarly obtained 3α-hydroxyisomer thereof has $R_f=0.550$.

night the solution is evaporated, the residue dissolved in 5 ml of water and 5 ml saturated aqueous sodium chloride, the mixture treated with dry-ice and extracted with diethyl ether. The extract is dried, evaporated, the residue dissolved in 80 ml of dry tetrahydrofuran and to the solution 350 ml of diethyl azodicarboxylate in 12 ml of tetrahydrofuran, 535 mg of triphenylphosphine and 230 mg of n-octanol, each in 12 ml of tetrahydrofuran, are added. The mixture is stirred at room temperature overnight, diluted with diethyl ether and washed with water and saturated aqueous sodium chloride. It is dried, evaporated, the residue dissolved in 8 ml of 60% aqueous acetic acid and the mixture stirred at room temperature over night. It is evaporated, the residue extracted with diethyl ether, the extract washed with water and 10% aqueous potassium bicarbonate, dried and evaporated. The residue is subjected to thin layer chromatography on silica gel, using ethyl acetate-methylene chloride (4:1) as eluant, to give the corresponding n-octyl ester having $R_f=0.236$.

I claim:

1. A 7-[3-hydroxy-3-hydrocarbylpropyl or -1-propenor ynyl)-4-hyroxy-tetrahydro-2β-thienyl]-alkanoic or 5-alkenoic acid of the formula

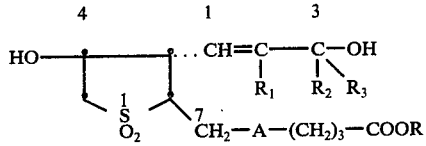

wherein R is hydrogen, an alkali metal, one equivalent of an alkaline earth metal, ammonium, mono-, di- or tri-lower alkylammonium, alkyl with up to 12 carbon atoms, lower alkenyl, lower alkynyl, Ph or Ph-$C_nH_{2n}$, wherein Ph is phenyl, (lower alkyl)-phenyl, (halogeno)-phenyl or (trifluoromethyl)-phenyl, and $n$ is an integer from 1 to 4, A is ethylene or ethenylene, each of $R_1$ and $R_2$ is hydrogen or lower alkyl and $R_3$ is alkyl with up to 12 carbon atoms, lower alkenyl or lower alkynyl, or the 1,2-dihydroderivatives or 1,2-dehydro-derivatives thereof.

2. A compound as claimed in claim 1, in which formula the hydroxy groups are 3α, 4α or 3β, 4β and R is hydrogen, sodium, potassium, lower alkyl or Ph'—$C_nH_{2n}$ wherein $n$ is an integer from 1 to 4 and Ph' is phenyl, tolyl, fluorophenyl or chloorophenyl, A is ethylene or cis-ethenylene, each of $R_1$ and $R_2$ are hydrogen or lower alkyl, and $R_3$ is lower alkyl, lower alkenyl, lower alkynyl or or Ph'-, 2.

3. A compound as claimed in claim 1 and corresponding to the formula

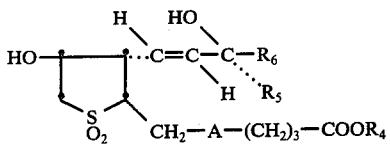

wherein $R_4$ is hydrogen, sodium, potassium or alkyl with up to 4 carbon atoms, A is ethylene or cis-ethylene, $R_5$ is hydrogen or methyl, $R_6$ is n-(butyl, pentyl, hexyl, heptyl or octyl) or 2-methyl-2n-(pentyl, hexyl or heptyl), 2.

4. A compound as claimed in claim 3, in which formula $R_4$ is hydrogen, sodium or potassium, A is ethylene or cis-ethenylene, $R_5$ is hydrogen or methyl, and $R_6$ is n-pentyl, n-hexyl or 2-methyl-2-n-hexyl or 5. A compound as claimed in claim 3 and being the 7-[1,1-dioxo-3α-(3β-hydroxy-1-trans-octenyl)-4β-hydroxy-tetrahydro-2β-thienyl]-heptanoic acid.

6. A compound as claimed in claim 3 and being the 7-[1,1-dioxo-3α-(3β-hydroxy-4,4-dimethyl-1-trans-octenyl)-4β-hydroxy-tetrahydro-2β-thienyl]-heptanoic acid.

7. A compound as claimed in claim 3 and being the 7-[1,1-dioxo-3α-(3β-hydroxy-4,4-dimethyl-1-trans-octenyl)-4β-hydroxy-tetrahydro-2β-thienyl]-5-cis-heptenoic acid.

* * * * *